US012674158B2

(12) United States Patent
Macheret et al.

(10) Patent No.: US 12,674,158 B2
(45) Date of Patent: Jul. 7, 2026

(54) METHODS FOR DNA LIBRARY GENERATION TO FACILITATE THE DETECTION AND REPORTING OF LOW FREQUENCY VARIANTS

(71) Applicant: Sophia Genetics S.A., Saint-Sulpice (CH)

(72) Inventors: Morgane Macheret, Saint-Sulpice (CH); Christian Pozzorini, Saint-Sulpice (CH); Adrian Willig, Saint-Sulpice (CH); Jonathan Bieler, Saint-Sulpice (CH); Zhenyu Xu, Saint-Sulpice (CH)

(73) Assignee: Sophia Genetics S.A., Rolle (CH)

( * ) Notice: Subject to any disclaimer, the term of this patent is extended or adjusted under 35 U.S.C. 154(b) by 934 days.

(21) Appl. No.: 17/438,461

(22) PCT Filed: Sep. 21, 2020

(86) PCT No.: PCT/EP2020/076246
§ 371 (c)(1),
(2) Date: Sep. 12, 2021

(87) PCT Pub. No.: WO2021/053208
PCT Pub. Date: Mar. 25, 2021

(65) Prior Publication Data
US 2022/0364080 A1 Nov. 17, 2022

(30) Foreign Application Priority Data

Sep. 20, 2019 (EP) ..................................... 19198542

(51) Int. Cl.
*C12N 15/10* (2006.01)
*C12Q 1/6869* (2018.01)

(52) U.S. Cl.
CPC ....... *C12N 15/1065* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 6,582,908 | B2 | 6/2003 | Fodor et al. |
| 8,209,130 | B1 | 6/2012 | Kennedy et al. |
| 9,850,523 | B1 | 12/2017 | Chudova et al. |
| 10,041,127 | B2 | 8/2018 | Talasaz |
| 2001/0053519 | A1 | 12/2001 | Fodor et al. |
| 2003/0152490 | A1 | 8/2003 | Trulson et al. |
| 2005/0122325 | A1 | 6/2005 | Twait |
| 2006/0199189 | A1 | 9/2006 | Bradford |
| 2011/0160078 | A1 | 6/2011 | Fodor et al. |
| 2012/0071331 | A1 | 3/2012 | Casbon et al. |
| 2012/0100548 | A1 | 4/2012 | Rava et al. |
| 2012/0136583 | A1 | 5/2012 | Lazar et al. |

| | | | |
|---|---|---|---|
| 2012/0165202 | A1 | 6/2012 | Porreca et al. |
| 2012/0214678 | A1 | 8/2012 | Rava et al. |
| 2014/0227705 | A1 | 8/2014 | Vogelstein et al. |
| 2016/0017419 | A1 | 1/2016 | Chiu et al. |
| 2016/0032396 | A1 | 2/2016 | Diehn et al. |
| 2016/0046986 | A1 | 2/2016 | Eltoukhy et al. |
| 2016/0053301 | A1 | 2/2016 | Raymond et al. |
| 2016/0319345 | A1 | 11/2016 | Gnerre et al. |
| 2017/0058332 | A1 | 3/2017 | Kermani et al. |
| 2019/0085406 | A1 | 3/2019 | Mortimer et al. |

FOREIGN PATENT DOCUMENTS

| | | |
|---|---|---|
| EP | 2893040 B1 | 7/2015 |
| EP | 3240911 B1 | 8/2020 |
| EP | 3766986 B1 | 6/2022 |
| EP | 3470533 B2 | 1/2023 |
| EP | 3443066 B1 | 10/2024 |
| EP | 4123032 B1 | 2/2025 |
| EP | 4488686 A3 | 4/2025 |
| GB | 2510725 B | 8/2015 |
| JP | 6275145 B2 | 2/2018 |
| JP | 2022548504 A | 11/2022 |
| WO | 2011155833 A2 | 12/2011 |
| WO | 2012024543 A1 | 2/2012 |
| WO | 2012042374 A2 | 4/2012 |
| WO | 2012088348 A2 | 6/2012 |

(Continued)

OTHER PUBLICATIONS

Notice of Reasons for Refusal of the Japan Patent Office in related Japanese Appl. No. 2022-512862, dated Nov. 19, 2024, 9 pages.
Brocks, D. et al., "Intratumor DNA methylation heterogeneity reflects clonal evolution in aggressive prostate cancer", Cell Rep, vol. 8 Issue No. 3, pp. 798-806, Aug. 7, 2014.
Chan, K. C. A. et al., "Noninvasive detection of cancer-associated genome-wide hypomethylation and copy number aberrations by plasma DNA bisulfite sequencing", PNAS, vol. 110 Issue No. 47, pp. 18761-18768, Nov. 19, 2013.
Chiu, R. W. K. et al., "Noninvasive prenatal diagnosis of fetal chromosomal aneuploidy by massively parallel genomic sequencing of DNA in maternal plasma", Proc Natl Acad Sci U S A, vol. 105 Issue No. 51, pp. 20458-20463, Dec. 23, 2008.

(Continued)

*Primary Examiner* — Juliet C Switzer
*Assistant Examiner* — Brian Ellis Young
(74) *Attorney, Agent, or Firm* — Bochner PLLC; Andrew D. Bochner; Caitlin A. Hyland

(57) ABSTRACT

Methods are disclosed for adding adapters to fragmented nucleic acids for next generation sequencing, including providing numerical codes based on variable adapter molecular barcode lengths on both sides of the fragmented nucleic acids and identifying reads from the same fragment based on both barcodes. The methods and products allow for the amplification of the fragmented nucleic acids when there is a low yield of isolated fragmented nucleic acids and also for efficient and reliable detection of low-frequency mutations including in subpopulations of cells within a subject.

15 Claims, 12 Drawing Sheets

Specification includes a Sequence Listing.

(56) References Cited

FOREIGN PATENT DOCUMENTS

| WO | 2012106559 A1 | 8/2012 |
| WO | 2012129363 A2 | 9/2012 |
| WO | 2012142213 A2 | 10/2012 |
| WO | 2012148477 A1 | 11/2012 |
| WO | 2013123442 A1 | 8/2013 |
| WO | 2013138510 A1 | 9/2013 |
| WO | 2013142389 A1 | 9/2013 |
| WO | 2013190441 A2 | 12/2013 |
| WO | 2014039556 A1 | 3/2014 |
| WO | 2014043763 A1 | 3/2014 |
| WO | 2014149134 A2 | 9/2014 |
| WO | 2014151117 A1 | 9/2014 |
| WO | 2014165549 A1 | 10/2014 |
| WO | 2014191938 A1 | 12/2014 |
| WO | 2015100427 A1 | 7/2015 |
| WO | 2015159293 A2 | 10/2015 |
| WO | 2015175705 A1 | 11/2015 |
| WO | WO2019180528 A1 * | 3/2018 |
| WO | WO2018144159 A1 * | 8/2018 |
| WO | 2019002366 A1 | 1/2019 |
| WO | 2019084245 A1 | 5/2019 |
| WO | 2019204702 A1 | 10/2019 |
| WO | 2020043803 A1 | 3/2020 |

OTHER PUBLICATIONS

Diehl, F. et al., "Analysis of mutations in DNA isolated from plasma and stool of colorectal cancer patients", Gastroenterology, vol. 135 Issue No. 2, pp. 489-498, Aug. 2008.

Diehl, F. et al., "Detection and quantification of mutations in the plasma of patients with colorectal tumors", Proc Natl Acad Sci U S A, vol. 102 Issue No. 45, pp. 16368-16373, Nov. 8, 2005.

Ding, L. et al., "Clonal evolution in relapsed acute myeloid leukaemia revealed by whole-genome sequencing", Nature, vol. 481 Issue No. 7382, pp. 506-510, Jan. 11, 2012.

Ehrich, M. et al., "Noninvasive detection of fetal trisomy 21 by sequencing of DNA in maternal blood: a study in a clinical setting", Am J Obstet Gynecol, vol. 204 Issue No. 3, pp. 205.e1-205e.11.

Fan, H. C. et al., "Noninvasive diagnosis of fetal aneuploidy by shotgun sequencing DNA from maternal blood", PNAS, vol. 105 Issue No. 42, pp. 16266-16271, Oct. 21, 2008.

Forshew, T. et al., "Noninvasive identification and monitoring of cancer mutations by targeted deep sequencing of plasma DNA", Sci Transl Med, vol. 4 Issue No. 136, pp. 1-12, May 30, 2012.

Fu, G. K. et al., "Counting individual DNA molecules by the stochastic attachment of diverse labels", PNAS, vol. 108 Issue No. 22, pp. 9026-9031, May 11, 2011.

Gerlinger, M. et al., "Intratumor Heterogeneity and Branched Evolution Revealed by Multiregion Sequencing", N Engl J Med, vol. 366 Issue No. 10, pp. 883-892, Mar. 8, 2012.

Hoey, T. "Drug resistance, epigenetics, and tumor cell heterogeneity", Sci Transl Med, vol. 2 Issue No. 28, pp. 1-3, Apr. 21, 2010.

Kinde, I. et al., "Detection and quantification of rare mutations with massively parallel sequencing", PNAS, vol. 108 Issue No. 23, pp. 9530-9535, May 17, 2011.

Kivioja, T. et al., "Counting absolute numbers of molecules using unique molecular identifiers", Nat Methods, vol. 9 Issue No. 1, pp. 72-74, Nov. 20, 2011.

Leary, R. J. et al., "Detection of chromosomal alterations in the circulation of cancer patients with whole-genome sequencing", Sci Transl Med, vol. 4 Issue No. 162, pp. 1-12, Nov. 28, 2012.

Narayan, A. et al., "Ultrasensitive measurement of hotspot mutations in tumor DNA in blood using error-suppressed multiplexed deep sequencing", Cancer Res, vol. 72 Issue No. 14, pp. 3492-3498, Jul. 15, 2012.

Newman, A. M. et al., "Integrated digital error suppression for improved detection of circulating tumor DNA", Nature Biotechnology, vol. 34, pp. 547-555, Mar. 28, 2016 (Abstract Only).

Pan, H. et al., "Epigenomic evolution in diffuse large B-cell lymphomas", Nat Commun, vol. 6, Issue No. 6921, pp. 1-12, Apr. 20, 2015.

Rizzo, J. M. et al., "Key principles and clinical applications of "next-generation" DNA sequencing", Cancer Prev Res (Phila), vol. 5 Issue No. 7, pp. 887-900, Jul. 2012.

Schmitt, M. W. et al., "Detection of ultra-rare mutations by next-generation sequencing", PNAS, vol. 109 Issue No. 36, pp. 14508-14513, Aug. 1, 2012.

Schwarzenbach, H. et al., "Cell-free nucleic acids as biomarkers in cancer patients", Nat Rev Cancer, vol. 11 Issue No. 6, pp. 426-437, Jun. 2011.

Sehnert, A. J. et al., "Optimal detection of fetal chromosomal abnormalities by massively parallel DNA sequencing of cell-free fetal DNA from maternal blood", Clin Chem, vol. 57 Issue No. 7, pp. 1042-1049, Jul. 2011.

Sharma, S. V. et al., "A chromatin-mediated reversible drug-tolerant state in cancer cell subpopulations", Cell, vol. 141 Issue No. 1, pp. 69-80, Apr. 2, 2010.

Shaw, J. A. et al., "Genomic analysis of circulating cell-free DNA infers breast cancer dormancy", Genome Res, vol. 22 Issue No. 2, pp. 220-231, Feb. 2012.

Stefansson, O. A. et al., "Epigenetic Modifications in Breast Cancer and Their Role in Personalized Medicine", The American Journal of Pathology, vol. 183 Issue No. 4, pp. 1052-1063, Oct. 2013.

Tsai, H. et al., "Discovery of rare mutations in populations: TILL-ING by sequencing", Plant Physiol, vol. 156 Issue No. 3, pp. 1257-1268, Jul. 2011.

Zill, O. A. et al., "Cell-free DNA next-generation sequencing in pancreatobiliary carcinomas", Cancer Discov., vol. 5 Issue No. 10, pp. 1040-1048, Jun. 24, 2015.

Extended European Search Report of the European Patent Office in related European Patent Appl. No. 25160115.9, dated Aug. 21, 2025, 10 pages.

Hawkins, J. A. et al., "Error-correcting DNA barcodes for high-throughput sequencing", bioRxiv, Retrieved from the URL: https://www.biorxiv.org/content/biorxiv/early/2018/05/07/315002.full.pdf, May 7, 2018, 23 pages.

* cited by examiner a)

b)

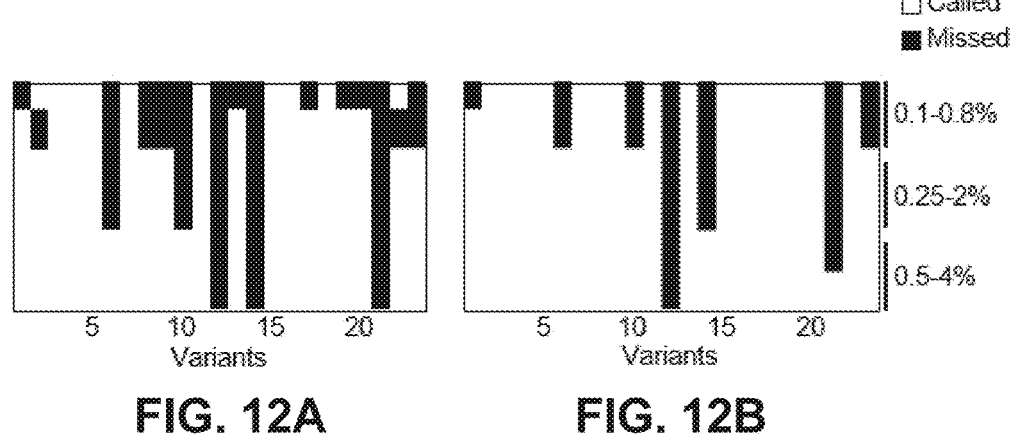
FIG. 12A
FIG. 12B
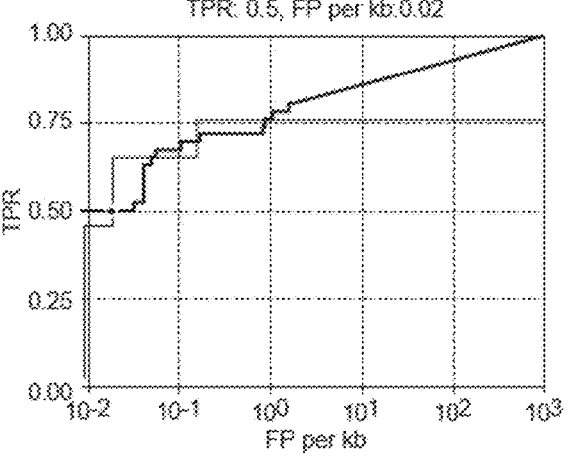
FIG. 12C
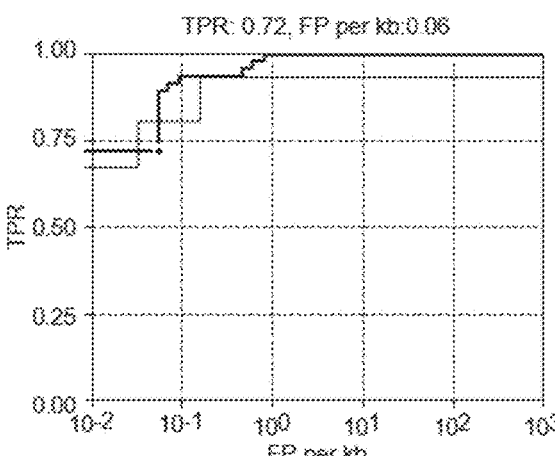
FIG. 12D

METHODS FOR DNA LIBRARY GENERATION TO FACILITATE THE DETECTION AND REPORTING OF LOW FREQUENCY VARIANTS

SEQUENCE LISTING

The instant application contains a Sequence Listing which has been submitted electronically in ASCII format and is hereby incorporated by reference in its entirety. Said ASCII copy, created on Jun. 3, 2022, is named 1200_017US_SL.txt and is 2,571 bytes in size.

BACKGROUND

Fields, such as cancer therapeutics, forensics, paleo-genomics, evolution and toxicology, require high-accuracy sequencing and detection of low incidence mutations. Such mutations might even be present in less than 1% of the cells, such as with cancer. When analyzing cell-free deoxyribonucleic acid (DNA) fragments from a plasma or blood sample, the ratio of DNA fragments from tumor cells may even be as low as 0.01% of the total cell-free DNA. This low incidence-genetic diversity is difficult to assess with conventional next generation sequencing due to a high background error rate not only in the sequencing itself, but in the amplification of the genomic DNA prior to sequencing. Circulating tumor DNA fragments may be fragmented to an average length of 140 to 180 bp (base pairs) and represent in only a few thousands amplifiable copies per millimeter of blood. DNA polymerases can introduce misinsertions at a frequency of $10^{-4}$ to $10^{-6}$. When these misinsertions occur early in the generation of the DNA library, such as during first strand synthesis, they can become indistinguishable from low-frequency mutations. Moreover, high throughput sequencing systems, also known as Next-Generation-Sequencing (NGS) systems typically produce errors at a per base rate of $10^{-2}$ to $10^{-3}$, making certain true variants undetectable when the corresponding mutations occur at a similar or lower frequency.

For example, single-cell sequencing, single-stranded molecular barcoding, and circle sequencing may involve sequencing DNA derived from a single strand of DNA. During the first round of amplification, DNA polymerase may propagate errors to the daughter molecules. In single-cell sequencing, random primers may be used with a DNA polymerase with helicase activity to displace one of the two strands. But the combination of random primers and strand displacement can result in random priming of the newly copied strand and thus, the generation of copies of copies. In the process, any initial misincorporation error will be passed to the copies of copies. As all the genetic information was derived from a single cell, it is impossible to tell whether the sequencing reads represent an error from the original single-strand synthesis or a genetic variant.

CircSeq and single-stranded barcoding may also introduce misinsertions during first round synthesis, an error which may then be propagated to daughter molecules and erroneously scored as a mutation. The same misinsertion error post-isolation is unlikely to occur in the same DNA sequence from other cells or sub-clonal populations. The original error therefore, could not necessarily be identified, accounted for, and/or corrected via post-hoc analysis, instead resulting in errors that may appear to be a sub-clonal mutations.

In *Enhancing the accuracy of next-generation sequencing for detecting rare and subclonal mutations*, Nature Reviews Genetics, Vol. 18, pp. 269-285, May 2018 Salk et al. review three main error correction strategies to better characterize low frequency variants with NGS technologies: 1) computational strategies based on filtering low confidence data and/or applying predefined statistical models of the sequencing error profiles 2) experimental strategies to reduce the errors caused by the pre-sequencing DNA library preparation and 3) molecular consensus sequencing, which applies a posteriori detection and correction of errors in the sequencing data reads themselves. The latter methods rely upon a unique tagging with a molecular barcode (also known as molecular tag, Unique Molecular Identifier UMI, or Single Molecular Identifier SMI) of each of the DNA fragments prior to amplification and sequencing, so that it is possible to group sequencing reads in families of reads associated with a specific tag. This facilitates the explicit detection and correction of errors introduced after the tagging, as it is unlikely that the very same error systematically repeats over all amplified and sequenced amplicon copies of the uniquely tagged parent DNA fragment. Salk et al. distinguish between exogenous molecular barcodes as random or semi-random sequences which are artificially (physically) incorporated into either the PCR primers or the sequencing adaptors on the one hand, and endogenous molecular barcodes which may be identified as naturally (virtually) occurring fragmentation points (also known as shear points) at the ends of DNA molecules when preparing the DNA library using ligation. Three main families of molecular consensus sequencing have been developed so far: 1) Single-Strand Consensus Sequencing, such as for instance the SafeSeqS, smMIP and CiqSed methods, which independently tags either one or both of the parent DNA fragment strands (thus with the limitation that it is not possible to use the strand information to group amplicon reads issued from complementary strands in the downstream consensus error detection and correction steps); 2) Two-Strand Consensus Sequencing, such as for instance the Ultrasensitive Deep Sequencing method or the CypherSeq method which tag both strands of the parent DNA fragment with the same molecular identifier so that the associated reads can be grouped into the same consensus sequence after sequencing; and 3) duplex sequencing, which introduces randomized duplex tags onto both ends of the original double-stranded DNA fragment in a complementary fashion. These molecular identifier sequences may be encoded into adaptors that are ligated to each end of a double-stranded DNA so that each end of the double-stranded DNA receives a different molecular identifier sequence. If an error is introduced by DNA polymerase into one of the two strands of DNA during first strand-synthesis or any subsequent synthesis/amplification step, the other strand provides a basis of comparison by, for example, reference to a set of single-stranded consensus sequences.

Once all the single strand consensus sequences are read during sequencing, the molecular identifier sequence on each end of each strand of the original DNA fragment can be matched during alignment.

To detect post-isolation errors which occur during synthesis steps subsequent to the first-synthesis step, each strand can be aligned with its same-strand sisters, by associating the sequencing reads sharing the same start and/or end positions during alignment of the single-strand consensus sequences using the molecular identifier sequence. Any differences in the read sequence can be attributed to misinsertions during a synthesis step subsequent to the first synthesis step. To detect post-isolation errors which occur during the first synthesis step, each strand can be aligned with its opposite-strand partner during alignment of the duplex consensus sequences (again, using the molecular identifier sequences). Any differences in the read sequences observed by such a comparison may be attributed to misinsertions during the first synthesis step. If a particular difference is found in both partner strands of the DNA with the same molecular identifier sequence at both ends of the DNA, then the particular difference may be attributed to a mutation or polymorphism existing in the DNA as extracted from the cell. Low incidence mutations in a subset of cells can be identified during the alignment of the total sequence readout by identifying strands with substantially similar sequences but having different molecular identifier sequences.

In *Error-correcting DNA barcodes for high-throughput sequencing*, J. A. Hawkins et al, bioRxiv, 7 May 2018 proposes the use of up to more than 10^6 unique error-correcting barcodes by constructing a library of DNA adaptors designed according to improvements over information theory codes such as Hamming codes, Reed-Solomon codes or Levenshtein codes. WO2018/144159 proposes the use of a variable length of 2 to 24 nucleotides with a constant 3 overhang to construct a library of DNA adaptors with another axis of diversity to facilitate the discrimination of the DNA sample fragment. Such methods may facilitate to a certain extent the inherent correction of substitution, insertion, and deletion errors, even when the corrupted length of the barcode is unknown, yet their specific design does not fully exploit the error correcting capability of the downstream sequencing data processing and variant calling workflows.

In *A review of somatic single nucleotide variant calling algorithms for next-generation sequencing data*, Computational and Structural Biotechnology Journal 16, pp. 15-24, Feb. 2018, Xu reviews 46 publicly available variant callers which may be applicable to single nucleotide variant detection, including 4 variant callers which handle UMI-based sequencing data possibly with duplex and consensus sequencing. As reported by Xu, one limitation of current duplex sequencing protocols is that in practical experiments, only 20% of the UMIs can be matched to the other strand due to insufficient ligation efficiency, so variant calling has to process both singular and duplex UMIs. Moreover, UMI sequences themselves are prone to PCR errors, which may require complementary clustering strategies.

There remains a need for improved methods of generating a DNA library which can be coupled to integrated low frequency variant identification, possibly independently from an explicit molecular barcoding consensus sequencing error identification/correction, e.g., by tracking both strands of a duplex DNA sample (such as genomic DNA fragments) to detect very low frequency mutations and polymorphisms. For example, there remains a need for efficient and reliable methods of detection of rare or low-frequency mutations and polymorphisms in cancer cells, chimeric cells, and other forms of intra-subject genetic polymorphisms. There also remains a need for improved methods of generating a DNA library which methods may track both strands of the same DNA molecule and facilitate the identification and reporting of multiple low frequency variants without the need for explicit consensus sequencing. There also remains a need for improved methods of producing asymmetric fragmented DNA libraries having different properties of the sequences on each end of a DNA fragment to be sequenced or analyzed.

SUMMARY

A method is proposed for generating a library of DNA-adaptor products from at least two DNA fragments, each DNA-adaptor product in the library allowing for identification and genomic variant analysis of its parent DNA fragment after amplification and sequencing, said method comprising ligating, in a reaction mixture, a first adaptor to one end and a second adaptor to the other end of a first double-stranded DNA fragment having two ends to produce a first DNA-adaptor product, each adaptor comprising a plurality of double-stranded or partially double-stranded polynucleotides, each double-stranded or partially double-stranded polynucleotide comprising a spacer sequence on the double-stranded extremity of the adaptor, the first adaptor spacer sequence ($SS_1$) having a length $L_1$ and the second adaptor spacer sequence ($SS_2$) having a length $L_2$; ligating, in the same reaction mixture, a third adaptor to one end and a fourth adaptor to the other end of a second double-stranded DNA fragment having two ends to produce a second DNA-adaptor product, each adaptor comprising a plurality of double-stranded or partially double-stranded polynucleotides, each double-stranded or partially double-stranded polynucleotide comprising a spacer sequence on the double-stranded extremity of the adaptor, the third adaptor spacer sequence ($SS_3$) having a length $L_3$ and the fourth adaptor spacer sequence ($SS_4$) having a length $L_4$, wherein each adaptor spacer sequence ($SS_1$, $SS_2$, $SS_3$, $SS_4$) comprises a spacer subsequence truncated from a common constant, predefined nucleotide sequence (S) of length $L_S$ nucleotides to produce adaptor spacer sequences, the adaptor spacer sequences ($SS_1$, $SS_2$, $SS_3$, $SS_4$) differing from each other by their lengths $L_1$, $L_2$, $L_3$, $L_4$ of at least 3 and at most $L_{max}$ nucleotides, $L_{max}$ being greater than or equal to $L_S$. The predefined nucleotide sequence length $L_S$ may be between 5 and 20 nucleotides. Each adaptor spacer sequence ($SS_1$, $SS_2$, $SS_3$, $SS_4$) may be formed by concatenating the truncated spacer subsequence with a constant termination subsequence TS having a constant length $L_{TS}$ of at least 3 nucleotides, the constant termination subsequence TS differing from the constant, predefined nucleotide sequence S by an edit distance of at least two. The spacer subsequence may either be truncated left to right from the start from the constant nucleotide sequence (S), or truncated right to left from the end from the constant nucleotide sequence (S). The constant termination subsequence TS may be a triplet nucleotide or a quadruplet nucleotide, preferably ending with a T overhang to facilitate ligation to the DNA fragments.

A method is proposed for generating a library of DNA-adaptor products from at least two DNA fragments to facilitate the identification of the fragments in a high throughput sequencing data genomic data analysis workflow after amplification and sequencing, comprising generating a pool of DNA-adaptors, wherein the adaptors differ from each other by their total lengths of at least 3 and at most $L_{max}$ nucleotides, wherein each adaptor comprises a constant termination subsequence TS of length $L_{TS}$, $L_{TS}$ 3 nucleotides concatenated with a variable spacer subsequence, and wherein the variable spacer subsequence is truncated from a common constant, predefined nucleotide sequence (S) having a length of $L_S$ nucleotides, 5 $L_S$ 20 nucleotides; ligating, in a reaction mixture, a first and a second adaptors from the pool of DNA-adaptors to each end of a first double-stranded DNA fragment to produce a first DNA-adaptor product, each adaptor comprising a plurality of double-stranded or partially double-stranded polynucleotides, each double-stranded or partially double-stranded polynucleotide comprising a spacer sequence on the double-stranded extremity of the adaptor, so that the first DNA-adaptor product may be characterized by a numerical code formed by the respective lengths ($L_1$, $L_2$) of the first and the second DNA-adaptor spacer sequences ($SS_1$, $SS_2$); and ligating, in the same reaction mixture, a third and a fourth adaptors from the pool of DNA-adaptors to each end of a second double-stranded DNA fragment to produce a second DNA-adaptor product, each adaptor comprising a plurality of double-stranded or partially double-stranded polynucleotides, each double-stranded or partially double-stranded polynucleotide comprising a spacer sequence on the double-stranded extremity of the adaptor, so that the first DNA-adaptor product may be characterized by a numerical code formed by the respective lengths ($L_3$, $L_4$) of the first and the second DNA-adaptor spacer sequences ($SS_3$, $SS_4$).

The DNA-adaptor products may be amplified to produce PCR duplicates and sequenced to produce raw sequencing reads. For each sequencing read $R_n$, a genomic data analyzer may trim $L_{max}=L_S+L_{TS}$ nucleotides from the beginning of the read to produce a trimmed sequencing read. The genomic data analyzer may search for the constant termination subsequence TS in the first $L_{max}$ nucleotides of the sequencing read, measure the length $L_n$ of the spacer sequence $SS_{Rn}$ as a function of the number of nucleotides separating the start of the constant termination subsequence TS from the start of the sequencing read $R_n$ and trim $L_n$ nucleotides from the beginning of the read to produce the trimmed sequencing read. The genomic data analyzer may record the trimmed sequencing read and possibly the measured length $L_n$ in a pre-processed sequencing read file, and align the trimmed sequencing reads to a reference genome so as to map each trimmed read to a start position and an end position. The genomic data analyzer may use the variable adaptor length information measured for each read to facilitate, with a consensus sequencing or a probabilistic sequencing bioinformatics method, the identification of genomic variants for the strand and the fragment, respectively.

BRIEF DESCRIPTION OF THE DRAWINGS

FIG. 5*a* discloses SEQ ID NOS 3, 2, and 1, respectively, in order of appearance.

FIG. 7 discloses SEQ ID NOS 6-8, and 6-8, respectively, in order of columns.

FIG. 12*a*) and FIG. 12*b*) compare the variant calling results obtained respectively when employing respectively prior art adaptors or the proposed variable length adaptors. FIG. 12*c*) and FIG. 12*d*) compare the ROC curves of a consensus sequencing workflow and of a probabilistic sequencing workflow when employing respectively prior art adaptors or the proposed variable length adaptors.

DETAILED DESCRIPTION OF THE INVENTION

Figure 1:
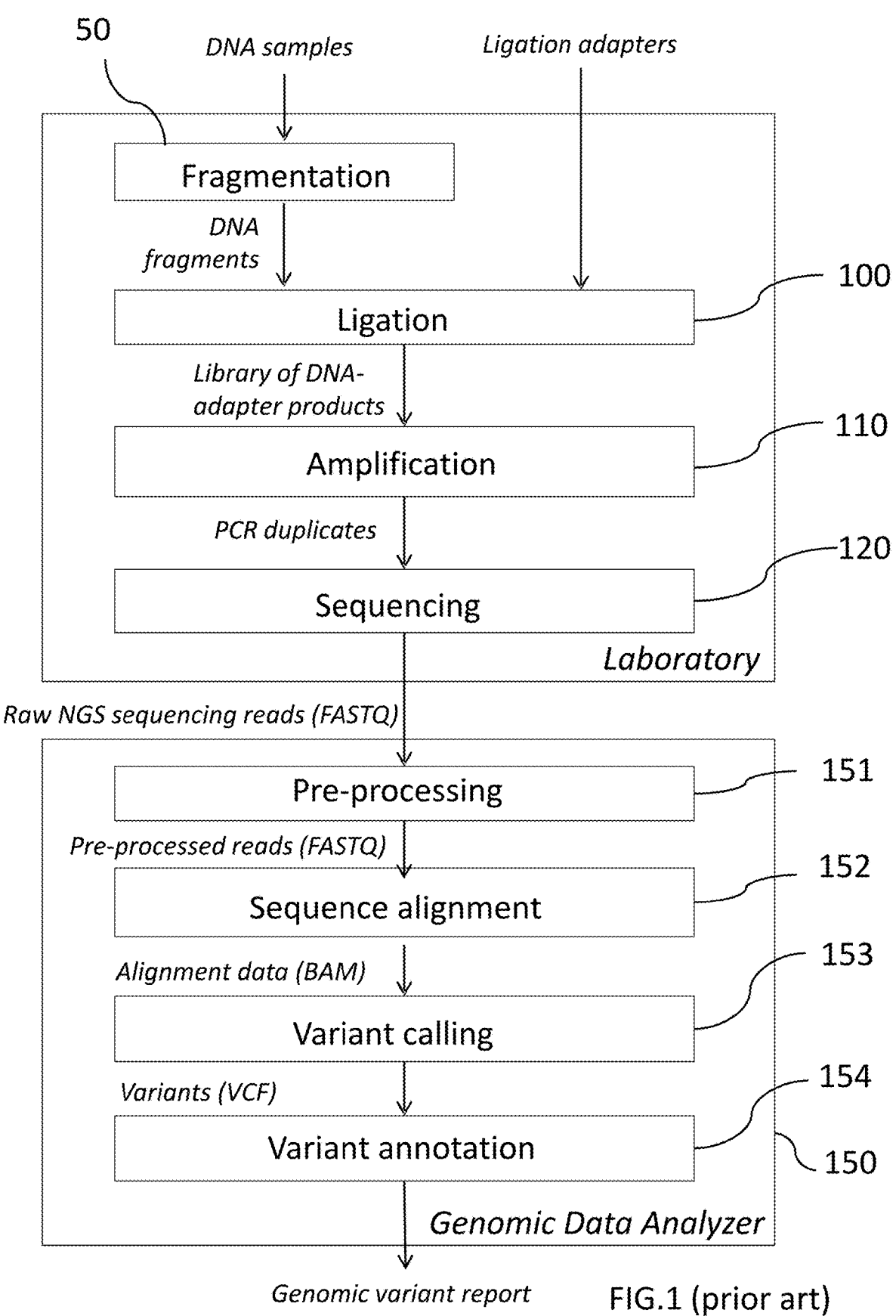
FIG. 1 is a schematic representation of a genomic analysis workflow comprising a tagging step with ligation adaptors for uniquely encoding the input DNA fragments into DNA-adaptor products in the laboratory process (also known as the wet lab process), and a pre-processing step on the resulting DNA-adaptor products sequencing reads to uniquely identify the DNA fragment source for each read in the bioinformatics workflow (also known as the dry lab process).

The particulars shown herein are by way of example and for purposes of illustrative discussion of the various embodiments only and are presented in the cause of providing what is believed to be the most useful and readily understood description of the principles and conceptual aspects of the methods and compositions described herein. In this regard, no attempt is made to show more detail than is necessary for a fundamental understanding, the description making apparent to those skilled in the art how the several forms may be embodied in practice.

The proposed methods and systems will now be described by reference to more detailed embodiments. The proposed methods and systems may, however, be embodied in different forms and should not be construed as limited to the embodiments set forth herein. Rather, these embodiments are provided so that this disclosure will be thorough and complete, and will fully convey the scope to those skilled in the art.

Unless otherwise defined, all technical and scientific terms used herein have the same meaning as commonly understood by one of ordinary skill in the art to which this invention belongs. The terminology used in the description herein is for describing particular embodiments only and is not intended to be limiting. As used in the description and the appended claims, the singular forms a, an, and the are intended to include the plural forms as well, unless the context clearly indicates otherwise.

Unless indicated to the contrary, the numerical parameters set forth in the following specification and attached claims are approximations that may vary depending upon the desired properties sought to be obtained and thus may be modified by the term about. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Definitions

A DNA sample refers to a nucleic acid sample derived from an organism, as may be extracted for instance from a solid tumor or a fluid. The organism may be a human, an animal, a plant, fungi, or a microorganism. The nucleic acids may be found in limited quantity or low concentration, such as fetal circulating DNA (cfDNA) or circulating tumor DNA in blood or plasma. A DNA sample also applies herein to describe RNA samples that were reverse-transcribed and converted to cDNA.

A DNA fragment refers to a short piece of DNA resulting from the fragmentation of high molecular weight DNA. Fragmentation may have occurred naturally in the sample organism, or may have been produced artificially from a DNA fragmenting method applied to a DNA sample, for instance by mechanical shearing, sonification, enzymatic fragmentation and other methods. After fragmentation, the DNA pieces may be end repaired to ensure that each molecule possesses blunt ends. To improve ligation efficiency, an adenine may be added to each of the 3 blunt ends of the fragmented DNA, enabling DNA fragments to be ligated to adaptors with complementary dT-overhangs.

A DNA product refers to an engineered piece of DNA resulting from manipulating, extending, ligating, duplicating, amplifying, copying, editing and/or cutting a DNA fragment to adapt it to a next-generation sequencing workflow.

A DNA-adaptor product refers to a DNA product resulting from ligating a DNA fragment with a DNA adaptor to adapt it to a next-generation sequencing workflow.

A DNA library refers to a collection of DNA products or DNA-adaptor products to adapt DNA fragments for compatibility with a next-generation sequencing workflow.

A pool refers to multiple DNA samples (for instance, 48 samples, 96 samples, or more) derived from the same or different organisms, as may be multiplexed into a single high-throughput sequencing analysis. Each sample may be identified in the pool by a unique sample barcode.

A nucleotide sequence or a polynucleotide sequence refers to any polymer or oligomer of nucleotides such as cytosine (represented by the C letter in the sequence string), thymine (represented by the T letter in the sequence string), adenine (represented by the A letter in the sequence string), guanine (represented by the G letter in the sequence string) and uracil (represented by the U letter in the sequence string). It may be DNA or RNA, or a combination thereof. It may be found permanently or temporarily in a single-stranded or a double-stranded shape. Unless otherwise indicated, nucleic acids sequences are written left to right in 5 to 3 orientation.

A random sequence or partially random sequence refers to a sequence of nucleotides which is at least in part randomly selected among all possible combinations of nucleotides for a given sequence length. The selection of the random sequence may be manual or automated.

A constant sequence or a predefined sequence refers to a fully specified, non-random, fixed sequence of nucleotides which is specifically selected among all possible combinations of nucleotides for a given sequence length. The selection of the non-random sequence may be manual or automated. The selection of the non-random sequence may be based upon certain criteria specific to the sequencing application and/or the sequencing technology, for instance to provide enhanced error robustness properties for amplification and sequencing steps.

A primer sequence refers to a nucleotide sequence of at least 20 nucleotides in length comprising a region of complementarity to a target DNA a part or all of which is to be elongated or amplified.

The edit distance between two sequences of nucleotides refers to the minimum number of nucleotide substitutions, insertions or deletions that needs to be applied for one sequence to become identical to the other sequence.

Ligation refers to the joining of separate double stranded DNA sequences. The latter DNA molecules may be blunt ended or may have compatible overhangs to facilitate their ligation. Ligation may be produced by various methods, for instance using a ligase enzyme, performing chemical ligation, and other methods.

Amplification refers to a polynucleotide amplification reaction to produce multiple polynucleotide sequences replicated from one or more parent sequences. Amplification may be produced by various methods, for instance a polymerase chain reaction (PCR), a linear polymerase chain reaction, a nucleic acid sequence-based amplification, rolling circle amplification, and other methods.

Sequencing refers to reading a sequence of nucleotides as a string. High throughput sequencing (HTS) or next-generation-sequencing (NGS) refers to real time sequencing of multiple sequences in parallel, typically between 50 and a few thousand base pairs. Exemplary NGS technologies include those from Illumina, Ion Torrent Systems, Oxford Nanopore Technologies, Complete Genomics, Pacific Biosciences, and others. Depending on the actual technology, NGS sequencing may require sample preparation with sequencing adaptors or primers to facilitate further sequencing steps, as well as amplification steps so that multiple instances of a single parent molecule are sequenced, for instance with PCR amplification prior to delivery to flow cell in the case of sequencing by synthesis.

An adapter or adaptor refers to a short double-stranded or partially double-stranded DNA molecule of around 10 to 100 nucleotides (base pairs) which has been designed to be ligated to a DNA fragment. An adaptor may have blunt ends, sticky ends as a 3 or a 5 overhang, or a combination thereof. For example, to improve ligation efficiency, an adenine may be added to each of the 3 blunt ends of the fragmented DNA prior to adaptor ligation, and the adaptor may have a thymidine overhang on the 3 end to base-pair with the adenine added to the 3 end of the fragmented DNA. The adaptor may have a phosphorothioate bond before the terminal thymidine on the 3 end to prevent an exonuclease from trimming the thymidine, thus creating a blunt end when the end of the adaptor being ligated is double-stranded.

A partially double stranded adaptor refers to an adaptor including both a double-stranded region and a single stranded region. The double stranded region of the adaptor contains the ligation domain, whereas the single stranded region contains the primering sequences used for subsequent library amplification, barcoding and/or sequencing. The single stranded region can either be composed of two single stranded arms, a 5 arm and a 3 arm, as it is the case for so-called Y-shape adaptors, or the single stranded region of partially double stranded adaptor can form a hairpin or a loop, as it is the case for the so-called U-shape adaptors. The term partially double stranded adaptor refers thus both to V-shape and U-shape adaptors or a combination thereof.

A PCR duplicate refers to a copy generated by PCR amplification from a single stranded DNA molecule belonging to a DNA-adaptor product derived from an original DNA fragment.

A molecular tag or molecular barcode or molecular code or molecular identifier refers to a molecular arrangement such as a nucleic acid sequence which is fully and uniquely specified by its string of nucleotides.

A numerical code or non-molecular code or non-molecular identifier refers to the measurement as one or more numerical values of an inherent property of a molecular arrangement, which is not the molecular arrangement itself. Examples of properties of a nucleic acid molecular sequence include length, size, molecular weight, molarity, polarity, elasticity, stiffness, electrical conductivity, fluorescence, reflectivity to certain excitation waves, or more generally any physical, chemical or biological property which may be experimentally measured for a molecular arrangement and/ or parts of a molecular arrangement.

A variable length code (VLC) refers to the variable length of a nucleic acid sequence which may be measured as the number of nucleotides, the number of monomers, the number of polymers, the number of homopolymers, the number of heteropolymers, or a combination thereof.

Read trimming or Read pre-processing refers, in a bioinformatics workflow, to the filtering out, in the sequencing reads, of a set of nucleotides at the start of the read sequence string, such as for instance the nucleotides corresponding to the adaptor sequences, to extract the real DNA fragment sequence to be analyzed.

Aligning or alignment or aligner refers to mapping and aligning base-by-base, in a bioinformatics workflow, the pre-processed sequencing reads to a reference genome sequence, depending on the application. For instance, in a targeted enrichment application where the sequencing reads are expected to map to a specific targeted genomic region in accordance with the hybrid capture probes used in the experimental amplificationprocess, the alignment may be specifically searched relative to the corresponding sequence, defined by genomic coordinates such as the chromosome number, the start position and the end position in a reference genome.

Variant calling or variant caller or variant call refers to identifying, in the bioinformatics workflow, actual variants in the aligned reads. Variants may include single nucleotide permutations (SNPs), insertions or deletions (INDELs), copy number variants (CNVs), as well as large rearrangements, substitutions, duplications, translocations, and others. Preferably variant calling is robust enough to sort out the real variants from the amplification and sequencing noise artefacts.

Consensus sequencing refers, in a bioinformatics workflow, to grouping sequencing reads into families of reads issued from the same double-stranded DNA fragment and/or the same DNA fragment strand, comparing them to detect errors due to the amplification and/or sequencing steps, and correcting the errors to produce a unique, deterministic consensus sequence for the double-stranded DNA fragment or the DNA fragment strand. Variant calling is then performed by processing the resulting consensus sequences, rather than the totality of reads.

Probabilistic sequencing refers, in a bioinformatics workflow, to grouping sequencing reads into families of reads issued from the same double-stranded DNA fragment and/or the same DNA fragment strand and performing variant calling directly on this data, by processing the totality of reads from different families in order to compute the probability of data supporting all the possible genotypes at each genomic position to be analysed, by comparing the data with a probabilistic model.

Workflow

An exemplary low frequency DNA variant identification workflow will now be described with further detail with reference to FIG. 1. As will be apparent to those skilled in the art of DNA analysis, such a workflow comprises preliminary experimental steps to be conducted in a laboratory (also known as the wet lab) to produce DNA analysis data, such as raw sequencing reads in a next-generation sequencing workflow, as well as subsequent data processing steps to be conducted on the DNA analysis data to further identify information of interest to the end users, such as the detailed identification of DNA variants and related annotations, with a bioinformatics system (also known as the dry lab). Depending on the actual application, laboratory setup and bioinformatics platforms, various embodiments of a DNA analysis workflow are possible. FIG. 1 describes an example of a workflow comprising a wet lab process wherein DNA samples are first fragmented with a fragmentation protocol 50 (optional) to produce DNA fragments. The DNA ends of these DNA fragments are then repaired and modified such as to be compatible with the adaptors that will be used. Adaptors as will be further described in more detail throughout this enclosure may then be joined by ligation 100 to the DNA fragments in a reaction mixture, so as to produce a library of DNA-adaptor products, in accordance with some of the proposed methods. The DNA library further undergoes amplification 110 and sequencing 120. In a next generation sequencing workflow, the resulting DNA analysis data may be produced as a data file of raw sequencing reads in the FASTQ format. The workflow may then further comprise a dry lab Genomic Data Analyzer system 150 which takes into input the raw sequencing reads for a pool of DNA samples prepared with the ligation adaptors according to the proposed methods, and applies a series of data processing steps to identify genomic variants, for instance as a genomic variant report for the end user. An exemplary Genomic Data Analyzer system 150 is the Sophia Data Driven Medicine platform (Sophia DDM) as already used by more than 1000 hospitals worldwide in 2019, but other systems may be used as well. Different detailed possible embodiments of data processing steps as may be applied by the Genomic Data Analyzer system 150 are described for instance in the international PCT patent application WO2017/220508, but other embodiments are also possible.

In a preferred embodiment, the Genomic Data Analyzer system 150 may first apply one or more pre-processing steps 151 to produce pre-processed reads from the raw sequencing reads inputs. The pre-processing steps may for instance comprise adaptor trimming, as well as read sorting, to analyze and group reads in families of reads issued from similar DNA fragments in accordance with the proposed adaptor ligation methods and numerical coding methods as will be further described herein. In a possible embodiment, the raw reads as well as the pre-processed reads may be stored in the FASTQ file format, but other embodiments are also possible. The Genomic Data Analyzer system 150 may further apply sequence alignment 152 to the pre-processed reads to produce read alignment data. In one embodiment, the read alignment data may be produced for instance in the BAM or SAM file format, but other embodiments are also possible.

The Genomic Data Analyzer system 150 may further apply variant calling 153 to the read alignment data to produce variant calling data. In one embodiment, the variant calling data may be produced for instance in the VCF file format, but other embodiments are also possible.

The Genomic Data Analyzer system 150 may further apply variant annotation 154 to the read alignment data to produce a genomic variant report for each DNA sample. In one embodiment, the genomic variant report may be visualized by the end user on a graphical user interface. In another possible embodiment, the genomic variant report may be produced as a text file for further data processing. Other embodiments are also possible.

Fragmentation

In some embodiments, methods as described herein will involve the use of genomic and mitochondrial DNA to be sequenced and determination of such information as the location and coding of genes, promoters, exons, introns, and potentially epigenetic information, such as CpG islands, and methylation, potentially in conjunction with bisulfide conversion. Genomic DNA may be chromosomal DNA or circular DNA. Alternately, mRNA may be reverse transcribed into complementary DNA or cDNA, and said cDNA may be fragmented, or it may be of a small enough length that it may be sequenced without fragmentation. The complementary cDNA, fragmented or non-fragmented, may be single-stranded, and could then be made double-stranded by annealing random primers and/or other primers and elongating the primers to be complementary to the cDNA, thus forming a double-stranded cDNA. In some embodiments, the double-stranded cDNA and mitochondrial and/or genomic DNA must be fragmented 50 prior to sequencing 120. Fragmentation 50 may be achieved by several means including but not limited to sonication, ultrasonication, mechanical shearing, partial digestion via for example restriction enzyme digestion, etc. Fragmentation may result in a fragmented DNA being 50 to 10000 base-pairs in length, preferably 200 base-pairs to 800 base-pairs in length, more preferably 300 to 500 base-pairs in length, and more preferably still 400 base-pairs in length. The DNA fragments, whether from cDNA, genomic DNA, or mitochondrial DNA, may be sized-fractionated, for example by agarose gel electrophoresis; gel chromatography; equilibrium density-gradient centrifugation, including sucrose gradient centrifugation, percol gradient centrifugation, cesium-chloride centrifugation; and other means.

Adaptor Ligation/Insertion

After fragmentation and end-repair 50, in the case of genomic DNA or chromosomal DNA or reverse transcription followed by formation of double-stranded DNA, adaptors may be ligated or linked 100 to each of the ends of the fragmented double-stranded DNAs.

Figure 2:
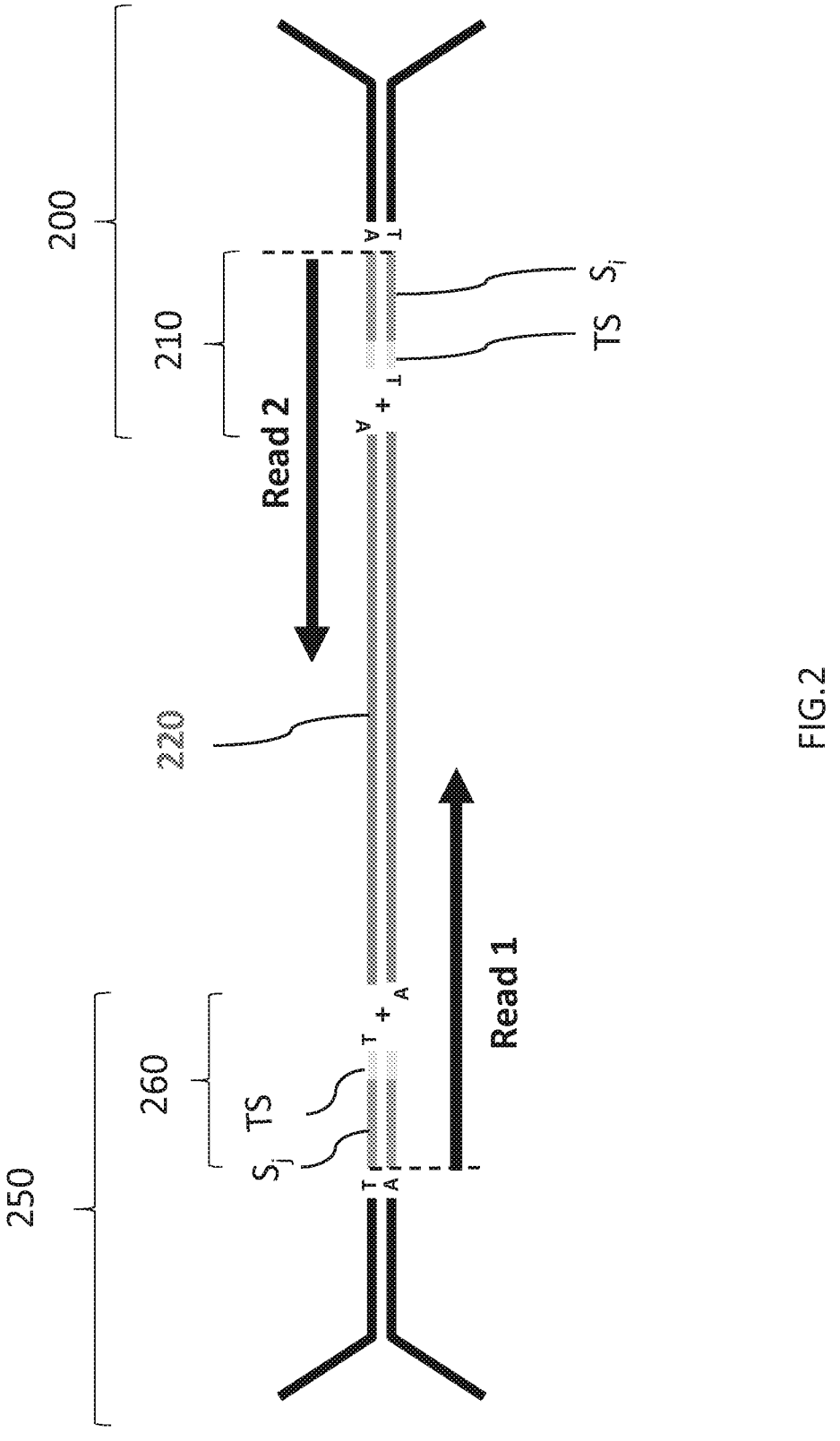
FIG. 2 is a schematic representation of an exemplary DNA-adaptor product for use in DNA library generation.

FIG. 2 shows an embodiment of the ligation 100 of two adaptors 200, 250 to each end of a DNA fragment 220. Each adaptor 200, 250 as shown in the exemplary embodiment as illustrated by FIG. 2 may comprise a partially double-stranded molecule of DNA with a single nucleotide (T) 3 overhang at the end to be annealed to the double-stranded fragmented DNA. Each adaptor 200, 250 comprises a double stranded segment 210, 260 at one end which constitutes a spacer sequence (SS) separating the adaptor 200, 250 from the DNA fragment 220 nucleotide sequences in subsequent high-throughput sequencing reads (Read1, Read 2). In a possible embodiment as illustrated by FIG.2, the latter spacer sequence end may contain a single-nucleotide T 3 overhang, but other embodiments are also possible as will be apparent to those skilled in the art, for instance it may be blunt ended or it may be substituted by another 3 or 5 overhang, so as to facilitate the ligation 100 of the adaptor 200, 250 to the target double stranded DNA molecules 220 (e.g., genomic DNA or gDNA).

An adaptor comprises a double-stranded sequence at the end being annealed to the double-stranded DNA. In this regard, one of the two strands of the double-stranded sequences of the adaptor will be ligated to the 3 end of the fragmented double-stranded DNA, and the other of the two strands of the double-stranded sequences of the adaptor will be ligated to the 5 end of the fragmented double-stranded DNA.

The ends of the double-stranded sequences of the adaptors being ligated to the fragmented double-stranded DNA are not limited and may comprise blunt ends, 3 overhangs, and 5 overhangs. In this regard, the 5 ends of the adaptors being ligated could either terminate with a 5-phosphate or a 5-OH. If a 5-OH is at the adaptor end to be ligated to the target nucleic acid, it may be necessary to use a polynucleotide kinase to complete the backbone and join the 5-OH of the adaptor to the 3-OH of the fragmented DNA. In some embodiments a one nucleotide overhang able to be ligated by T-4 ligase from the T-4 bacteriophage is preferable. Thus, in some embodiments, an adenine may be added to each of the 3 blunt ends of the fragmented DNA prior to adaptor ligation, and the adaptor may have a thymidine overhang on the 3 end to base-pair with the adenine added to the 3 end of the fragmented DNA. In some embodiments, an adenine may be added to each of the 3 blunt ends of the fragmented DNA prior to adaptor ligation, and the adaptor may have a phosphorothioate bond before the terminal thymidine on the 3 end to base-pair with the adenine added to the 3 end of the fragmented DNA. The phosphorothioate bond before the terminal thymidine will prevent an exonuclease from trimming the thymidine, thus creating a blunt end when the end of the adaptor being ligated is double-stranded.

Adaptors With Variable Length Spacer Sequence

In a preferred embodiment, as illustrated on FIG. 2, each adaptor 200, 250 comprises a spacer sequence 210, 260 terminating its double-stranded end to be linked to the DNA fragment 220. In one embodiment, part or all of the spacer sequence 210, 260 may be truncated from a predefined, constant nucleotide sequence S of length $L_S$ nucleotides to form a diversity of variable length truncated spacer subsequences $S_i$, $S_j$.

In one embodiment, in order to facilitate downstream read trimming pre-processing 151 by the genomic data analyzer 150 out from the raw sequencing reads, each truncated spacer subsequence $S_i$, $S_j$ of respective lengths $L_{Si}$, $L_{Sj}$ of at most $L_S$ nucleotides may be followed by a constant termination subsequence TS of a length $L_{TS}$ at least 3 nucleotides, for instance by concatenating each truncated variable length subsequence $S_i$, $S_j$ with the TS termination subsequence, to form the variable length spacer sequences 210, 260, as illustrated on FIG. 2.

Preferably, the predefined, constant nucleotide sequence S and the constant termination subsequence TS are chosen such that the constant termination subsequence TS differs from the reminder of the sequence S by an edit distance of at least two. As illustrated by FIG. 2, each adaptor spacer sequence SS 210, 260 may thus be terminated by the same, constant termination subsequence TS of at least 3 nucleotides, the termination subsequence TS differing from the reminder of the sequence S (and thus from any of its derived truncated spacer subsequences $S_i$, $S_j$) by an edit distance of at least two.

Figure 3:
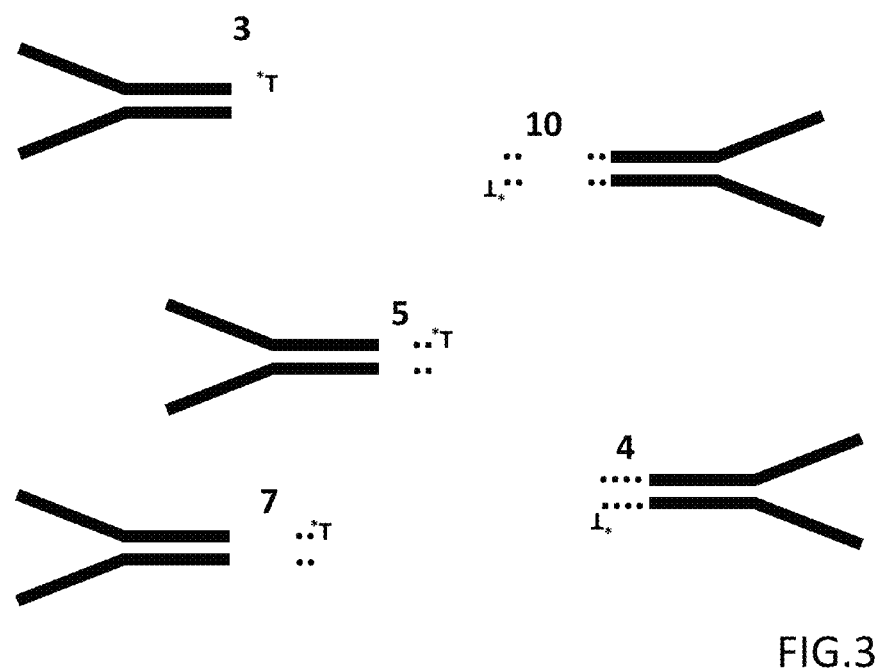
FIG. 3 shows a diversity of adaptors with a variable length spacer sequence partially truncated from a predefined constant sequence as may be used in the proposed method.

As illustrated by FIG. 3, a plurality of adaptors may be used, differing from each other specifically by the length of their truncated spacer subsequence $S_i$, $S_j$. The resulting total length for the spacer sequence 210, 260 once concatenated with a constant termination subsequence TS may thus be for example 3 nucleotides (as is the minimal size for a termination subsequence which may be used as a triplet stop code to facilitate downstream read trimming pre-processing 151), 10 (7+3) nucleotides, 5 (2+3) nucleotides, 7 (4+3) nucleotides, 4 (1+3) nucleotides More generally, the spacer sequence variable length may be at least $L_{TS}=3$ nucleotides, and at most $L_{max}=L_S+L_{TS}$ nucleotides. Similarly, for a quadruplet termination subsequence TS, the spacer sequence variable length may be at least $L_{TS}=4$ nucleotides, and at most $L_{max}=L_S+L_{TS}$ nucleotides, etc.

In general, the maximal length $L_S$ of the constant polynucleotide sequence S may be chosen such that the derived spacer sequence 210, 260 does not take too long a segment relative to the total sequencing read length (which may be as low as 150 base pairs in some high throughput sequencing workflows) while enabling enough different variable truncated lengths to provide the required combinatorial diversity to discriminate PCR duplicates from similar DNA fragments from the bioinformatics workflow point of view, that is fragments which share the same reference mapping positions once ligated with a couple of adaptors out of the plurality of adaptors with different truncated lengths. In a possible embodiment, $L_S$ may be chosen as 5, 6, 7, 8, 9, 10, 11, 12, 13, 14, 15, 16, 17, 18, 19 or 20 nucleotides, but other embodiments are also possible. When preparing a pool of samples for high throughput sequencing, in a possible embodiment the same constant polynucleotide sequence S may be used to prepare the ligation adaptors for all samples in a pool of samples to be multiplexed together in the NGS workflow; in an alternate embodiment different constant polynucleotide sequences may be defined and used to prepare the ligation adaptors for different samples in the same pool. In the latter embodiment, the plurality of adaptors produced for each sample in the pool of samples may differ by either the predefined termination subsequence (TS) or the predefined nucleotide sequence (S) used for truncating for the variable spacer subsequence. The choice of (TS, S) is thus common and constant for all fragments of a sample, but differs from one sample to another in the same pool.

Figure 4:
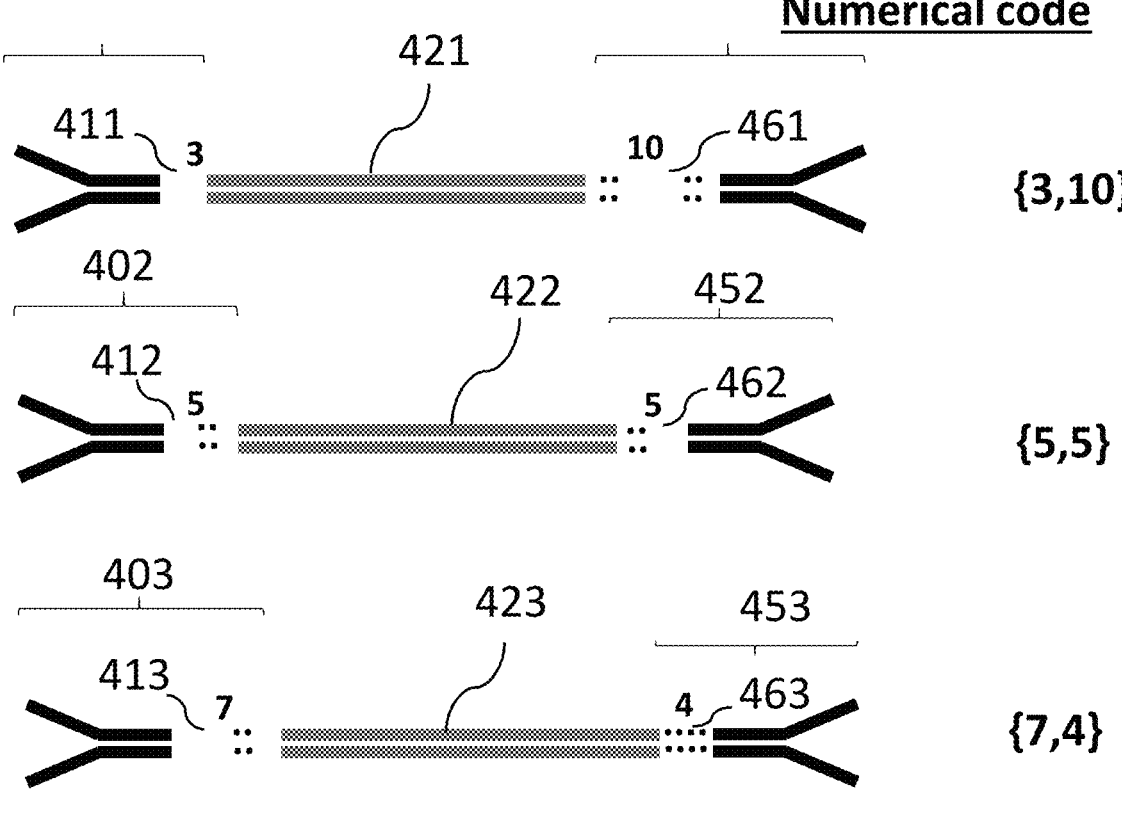
FIG. 4 illustrates examples of numerical codes as may be generated by the proposed method for the DNA-adaptor products associated with each DNA fragment.

FIG. 4 illustrates the resulting ligation and corresponding numerical code for three exemplary DNA fragments 421, 422, 423. The first DNA fragment 421 is ligated to a first adaptor 401 comprising a spacer sequence 411 (SS$_1$) having a total length $L_1$ of 3 nucleotides on one end and to a second adaptor 451 comprising a spacer sequence 461 (SS$_2$) having a total length $L_2$ of 10 nucleotides on its other end. The second DNA fragment 422 is ligated to a third adaptor 402 comprising a spacer sequence 412 (SS$_3$) having a total length $L_3$ of 5 nucleotides on one end and to a fourth adaptor 452 comprising the same spacer sequence 462 (SS$_4$ note that in this specific example SS$_4$=SS$_3$) having a total length $L_4$=$L_3$=5 nucleotides on its other end. The third DNA fragment 423 is ligated to a fifth adaptor 403 comprising a spacer sequence 413 (SS$_5$) having a total length $L_5$ of 7 nucleotides on one end and to a sixth adaptor 453 comprising a spacer sequence 463 (SS$_6$) having a total length $L_6$=4 nucleotides on its other end. The first DNA-adaptor product issued from DNA fragment 421 may thus be associated with a numerical code {3,10} (or {10,3} depending on the read direction) corresponding to the respective lengths of the spacer sequences from its adaptors on both ends. The second DNA-adaptor product issued from DNA fragment 422 may thus be associated with a numerical code {5,5} (in any read direction) corresponding to the respective lengths of the spacer sequences from its adaptors on both ends. The third DNA-adaptor product issued from DNA fragment 423 may thus be associated with a numerical code {7,4} (or {4,7} depending on the read direction) corresponding to the respective lengths of the spacer sequences from its adaptors on both ends. It is thus possible to discriminate between the first, second and third DNA-adaptor products with identical mapping positions in a DNA library and to trace back the derivative DNA products from each parent DNA-adaptor product by identifying the spacer sequences on both ends of the derivative DNA products and measuring their respective lengths to identify the numerical code inherited from the parent DNA-adaptor product.

Figures 5A, 5B:
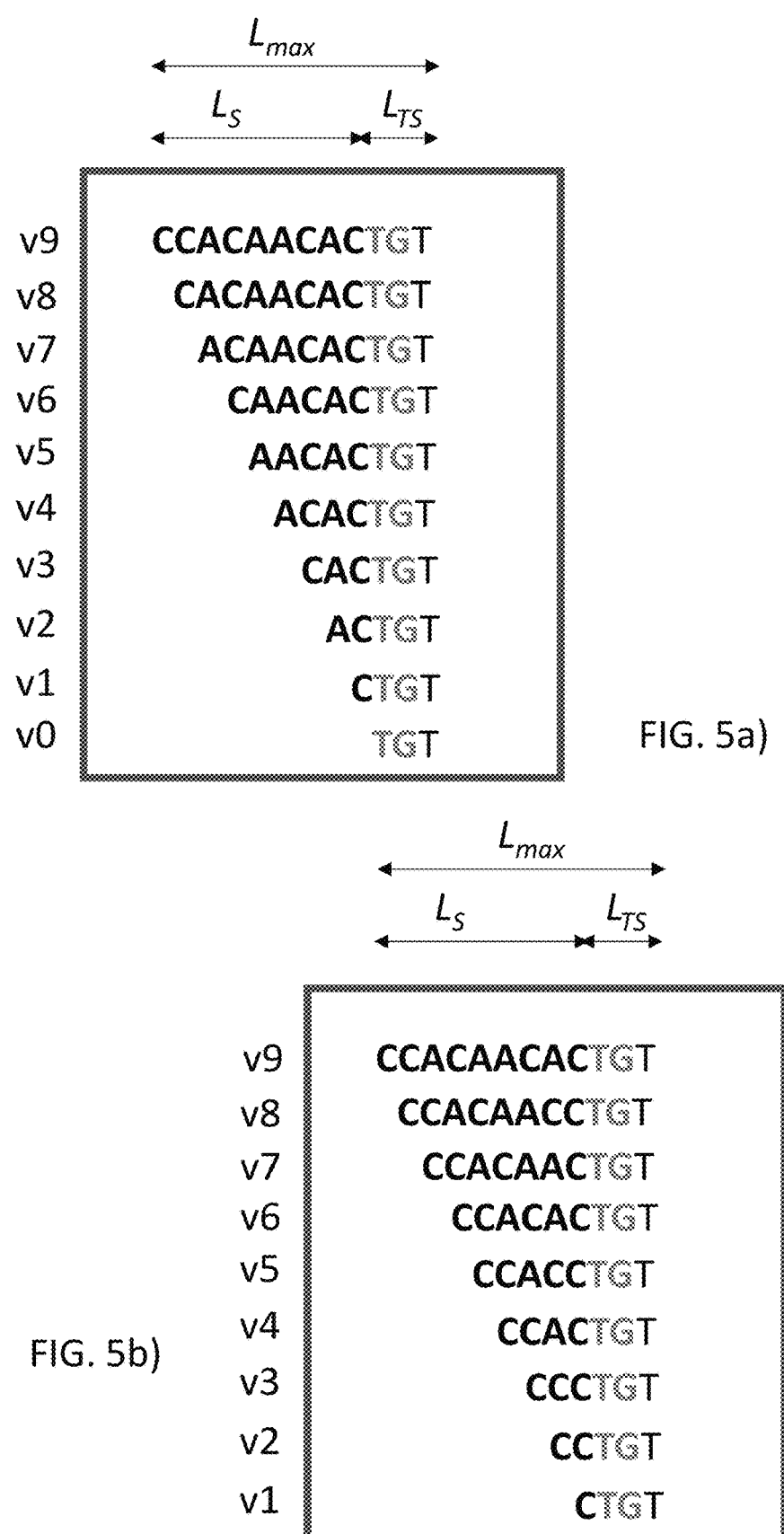
FIG. 5*a*) and FIG. 5*b*) each show an example of a set of spacer sequences SS formed by concatenating variable length truncated spacer subsequences derivatives $S_i$ with a termination sequence for producing the adaptors to be used with the proposed method.
FIG. 5*b* discloses SEQ ID NOS 3, 4, and 5, respectively, in order of appearance.

FIG. 5a) illustrates a first example of ten possible spacer sequences identified in FIG. 5a) as v9, v8, v7, v6, v5, v4, v3, v2, v1, v0. Each spacer sequence may be formed by the truncation left to right from the start of a constant sequence S=CCACAACAC of length $L_S$=9, further concatenated with a termination subsequence (TS) triplet T, G, T (itself ending with a T overhang to facilitate the ligation). FIG. 5b) illustrates an alternate, second example of ten possible spacer sequences which may be truncated right to left from the end of a constant sequence S=CCACAACAC of length $L_S$=9, further concatenated with a termination susbsequence (TS) triplet T, G, T (itself ending with a T overhang to facilitate the ligation). In both examples of FIG. 5a) and FIG. 5b), the constant sequence S=CCACAACAC is of length $L_S$=9 and each possible derived truncated subsequence has a subsequence length of 9, 8, 7, 6, 5, 4, 3, 2, 1 and 0 nucleotide respectively. When followed by a triplet of T, G, T nucleotides, which will correspond to a triplet code TGT in the resulting sequencing reads, the resulting spacer sequence total lengths are then respectively 12, 11, 10, 9, 8, 7, 6, 5, 4, and 3 nucleotides.

In a possible embodiment, the full spacer sequence length of the truncated plus termination subsequences (absolute length, for instance numerical in the range values 3 to 12) may be used to form the numerical code. In an alternate embodiment the sole length of the truncated subsequence part of the spacer sequence, thus excluding the constant length of the termination subsequences, may be used to form the numerical code (relative length, for instance numerical values in the range 0 to 7).

Amplification and Sequencing

Once the DNA products have been produced with adaptor ligation, they may be amplified by a polynucleotide amplification reaction to produce multiple polynucleotide sequences replicated from one or more parent sequence. As will be apparent to those skilled in the art of next generation sequencing, amplification may be produced by various methods, for instance a polymerase chain reaction (PCR), a linear polymerase chain reaction, a nucleic acid sequence-based amplification, rolling circle amplification, and other methods. In some embodiments, after library amplification, DNA-adaptor products can then be sequenced using any technology known in the art including, but not limited to, the Illumina sequencing technology, the Ion Torrent sequencing technology, the 454 Life Sciences sequencing technology, the ABI SOliD sequencing technology, the Pacific Biosciences sequencing technology or the Oxford nanopore sequencing technology. For example, in the case of the Illumina sequencing platform, the sequencer primering sequences present on both ends of library products have the functional property of annealing or binding to the flow cell oligomers or flow cell sequences. As will be apparent to those skilled in the art of next generation sequencing, a bridge-amplification process 110 may then be carried out wherein the fragmented DNA comprising the adaptor sequences (including the spacer sequences), the first primering sequences, and the second primering sequences will be annealed to either a first and/or second immobilizer sequences. The 3-OH of the first and/or second immobilizer sequences will then be elongated, using the fragmented DNA comprising the adaptor sequences, the first primering sequence, and the second primering sequence, as a template the genetic information within the fragmented DNA comprising the adaptor sequences (including the proposed spacer sequences), the first primering sequence, and the second primering sequence will thus be transferred to the first or second immobilizer sequences and thus bound to the solid state support. The fragmented DNA comprising the adaptor sequences (including the proposed spacer sequences), the first primering sequences, and the second primering sequences will then be denatured or deannealed and removed. The bound fragmented DNA will then be annealed to the immobilizer sequence at the free end of the bound fragmented DNA and undergo several cycles of bridge amplification.

At this point in time, the cluster generation process has been completed and the flow cell is configured in such a way as to permit sequencing by synthesis 120 by the reannealing of the free immobilizing sequence to the cleaved and therefore free immobilizer sequence. After priming, each nucleotide may be incorporated into the newly synthesized strand of DNA based on the template strand annealed to the solid state support during cluster generation. Each nucleotide being incorporated into the newly synthesized strand is associated with a different fluorophore, and each fluorophore may emit a different wave-length of light when the newly incorporated nucleotide may be integrated into the new strand of DNA and/or base-pairs with its complementary counterpart (A to T, G to C) during elongation.

In exonuclease based nanopore sequencing the nucleic acid may be digested and the produced free nucleotides will be identified by their effect on the electric potential across a lipid a membrane. A single stranded nucleic acid strand might also be forced to pass through a nanopore driven by differences in the electric potential or assisted by enzymes such helicases or a polymerases. The movement of the nucleic acid strand through the nanopore may produce a change in electric potential allowing the identification of the nucleic acid sequence.

The index sequence may then be used to identify the samples of the sequences. After read pre-processing 151 and read alignment 152, PCR duplicates can be identified using the DNA fragment endogenous information and/or mapping positions, the DNA fragment exogenous mapping positions or a combination thereof to distinguish true mutants from misinsertions caused after the DNA fragmentation.

In some embodiments, during the polymerization or elongation of a new strand of DNA from a template strand, DNA polymerase will sometimes incorrectly position a base which does not base-pair with the nucleotide opposite it on the other strand of DNA this is referred to as a mismatch or misinsertion. In this regard, the newly synthesized strand of DNA may be considered to be complementary to the template strand, even though one or several mismatches may occur. In embodiments, it is contemplated that this mismatching error by DNA polymerase may occur in a daughter strand of DNA, and that tracking all the copies belonging to the same PCR duplicate group as this daughter strand may permit discrimination of these mismatches from genetic polymorphisms (e.g. mutations) found in the genomic DNA as extracted from the cell.

Read Pre-Processing

Figure 6:
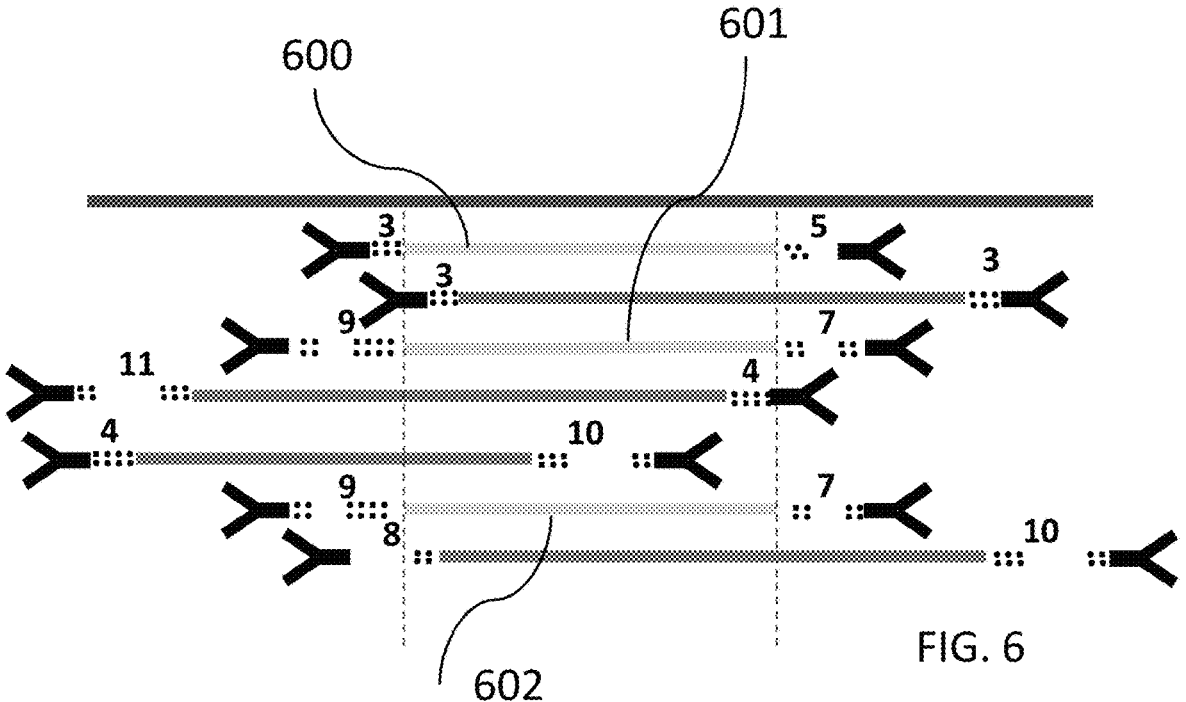
FIG. 6 illustrates an example of various DNA-adaptor PCR duplicates at the sequencing stage, out of which two duplicates can be traced back to the same parent DNA product thanks to their unique numerical codes as may be generated by the proposed method for the DNA-adaptor products associated with each DNA fragment.

After amplification 110, each DNA-adaptor product is replicated in a plurality of PCR duplicates. As illustrated on FIG. 6, two PCR duplicates 601, 602 issued from the same DNA-adaptor product, that is from the same DNA fragment, will thus have the same start and end coordinates and carry the same spacer sequences on their ends, which will be found in the resulting raw sequencing reads after sequencing 120. It is therefore possible to group them together in the downstream genomic analysis workflow by measuring the respective lengths of their spacer sequences (numerical code=$\{9,7\}$ in the example of FIG. 6).

As will be appreciated by those skilled in the art of low frequency DNA analysis, PCR duplicates issued from other DNA-adaptor products, that is from different DNA fragments, are unlikely to carry the same spacer sequences lengths provided that 1) the number of different possible adaptor combinations is large enough relative to the number of possibly colliding DNA fragments to discriminate out of the reads with the same start and end positions after alignment 152 and 2) the PCR amplification and sequencing errors, including possible insertion or deletion of nucleotides in the spacer sequence, can be detected thanks to the use of a constant sequence S as the basis for the truncated spacer subsequences to be retrieved in the reads.

As illustrated on FIG. 2, in the case of pair-end sequencing technology, after sequencing two different read directions READ1 and READ2 may each generate a different spacer sequence yet with a common termination sequence TS in the FASTQ file, but this spacer sequence may have a different length for each DNA-adaptor product, thus enabling to statistically distinguish it from another one. In the alignment 152 step, the start and the end positions of the DNA fragment sequence 220 to analyze will be thus shifted apart among most of the reads issued from different DNA-adaptor products, thus creating further endogenous diversity.

For instance, with reference to FIG. 4, for the first DNA fragment 421 a first spacer sequence 411 will constitute the first 3 nucleotides in the raw sequencing reads for PCR duplicates read from 3 to 5 direction, while the second spacer sequence 461 will constitute the first 10 nucleotides in the raw sequencing reads for the same PCR duplicates read in the reverse 5 to 3 direction. For the second DNA fragment 422 the third spacer sequence 412 will constitute the first 5 nucleotides in the raw sequencing reads for PCR duplicates read from 3 to 5 direction, and the fourth spacer sequence 462 will constitute the first 5 nucleotides in the raw sequencing reads for the same PCR duplicates read in the reverse 5 to 3 direction. For the third DNA fragment 423 the fifth spacer sequence 413 will constitute the first 7 nucleotides in the raw sequencing reads for PCR duplicates read from 3 to 5 direction, and the sixth spacer sequence 463 will constitute the first 4 nucleotides in the raw sequencing reads for the same PCR duplicates read in the reverse 5 to 3 direction. It is thus possible to uniquely associate a numerical code to each DNA fragment: the combination $\{L_1, L_2\}=\{3, 10\}$ of the spacer sequence length values for respectively the first end and the second end of the first DNA fragment 421; the combination $\{L_3, L_4\}=\{5, 5\}$ of the spacer sequence length values for respectively the first end and the second end of the second DNA fragment 422; the combination $\{L_5, L_6\}=\{7, 4\}$ of the spacer sequence length values for respectively the first end and the second end of the third DNA fragment 423, etc. As illustrated by FIG. 4, it is thus possible to group the PCR duplicate raw sequencing reads based on the variable length of the spacer sequences as can be retrieved from their start sequence of nucleotides in the raw sequencing reads sequenced from the PCR duplicates issued from the DNA-adaptor products generated with the proposed method.

Figure 7:
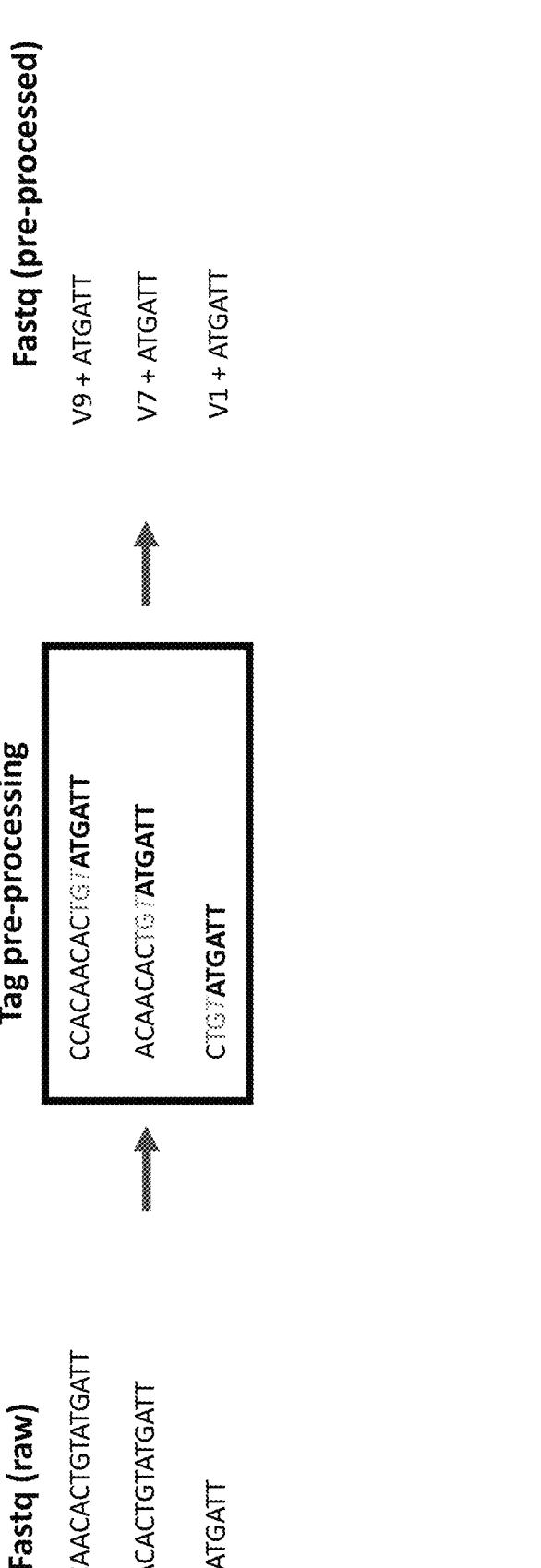
FIG. 7 shows an example of pre-processing the raw sequencing reads to identify the source DNA fragment and to tag each read accordingly.

FIG. 7 provides examples of the start sequences for three different reads as may be issued from the sequencing of the DNA-adaptor products constructed according to the exemplary sequences of FIG. 5a). Each spacer sequence ends with the termination sequence triplet TGT as in the example of FIG. 5a), so it is possible for the Genomic Data Analyzer 150 to search for this triplet as part of the read pre-processing step 151.

In a first possible embodiment (not illustrated), the read pre-processing 151 consists in first trimming the read start sequence by $L_{max}$ nucleotides, $L_{max}$ being the sum of the length $L_S$ of the constant sequence S out from which the subsequences are truncated and of the length $L_{TS}$ of the concatenated constant termination subsequence TS. After trimming the reads in the FASTQ file the remainder of the sequence for each read may be stored in a pre-processed FASTQ file.

As will be apparent to those skilled in the art of sequencing, due to the use of variable length adaptors, the resulting pre-processed reads will be shifted relative to each other with different start and end positions after subsequent alignment 152, which will de facto statistically separate the alignment results issued from different DNA-adaptor products. The latter endogenous length discrimination may however not be statistically sufficient to discriminate between the DNA fragments to be analyzed, depending on the actual application needs. Moreover, it has the drawback of losing a few nucleotides at the start of the fragment due to trimming to the length of the longest possible adaptor even for the reads carrying shorter truncated spacer subsequences.

Therefore, in alternate embodiment, the termination subsequence TS may be searched at the start of each read sequence. Once it is found, the length of the spacer sequence string may be measured, for instance as the distance between the start of the read and the start of the termination subsequence TS (relative spacer sequence SS length). Alternately, it may be measured as the distance between the start of the read and the end of the termination subsequence TS (absolute spacer sequence SS length). Each read may thus be assigned a different spacer sequence length measurement as part of the read pre-processing 151 step. In the example of FIG. 7, the first read carries at the beginning the spacer sequence $SS_1$=CCACAACACTGT (SEQ ID NO: 3) of absolute length $L_1$=12;

The second read carries the spacer sequence $SS_2$=ACAACACTGT (SEQ ID NO: 1) of absolute length $L_2$=10, and the third read carries the spacer sequence $SS_3$=CTGT of absolute length $L_3$=4. The measured length value may thus be recorded in the pre-processed FASTQ file so as to provide an extra numerical information enabling to trace back the DNA-adaptor product origin of the read in the downstream alignment process 152. Thus, depending on the actual needs of the application, the read sequence remainder to be input to the alignment may be either generically trimmed to the length $L_{max}$ of the longest possible spacer sequence, so as to provide a further endogenous length discrimination to the alignment process (yet at the expense of losing a few nucleotides at the beginning of the fragment sequence itself), or alternately it may be individually trimmed to the actual spacer sequence SS length $L_n$ as measured for each sequencing read $R_n$ by the pre-processing 151 (until the end of the termination sequence TS).

Read Mapping and Alignment

The resulting pre-processed reads may then be aligned 152 to a reference genome. It is then possible to discriminate in the data records (typically stored as BAM or SAM file formats) the set of reads issued from PCR duplicates of different original DNA fragments based on one or more of the following features available in the data records:

1) The numerical code obtained by combining the adaptor spacer sequence lengths measured in the reads;
2) The mapping position (i.e., start-end) of the DNA fragment, relative to the reference genome.

In the case of pair-end sequencing, the pair-end read orientation information (i.e., F1R2 or F2R1), which allows to discriminate pair-end reads issued from the original plus or minus strand may be used. For each couple of pair-end reads (i.e., R1 and R2) it is possible to recover their possibly different adaptor lengths and use these numbers to form a numerical code (composed of a pair of integer values) to be stored as a tag in a read alignment file, such as a BAM format file. In a first step, pair-end reads aligned to the same start and end position (relative to the reference genome sequence reading direction) and having the same pair of measured adaptor lengths (L1, L2) or (L2, L1) may be grouped as sequencing reads possibly issued from the two strands of the same original double-stranded DNA fragment. Then each group may be further subdivided in two subgroups according to their strand of origin, where the actual pair of measured adaptor lengths (L1, L2) is given by $\{L_{n\ (forward)}, L_{m\ (reverse)}\}$ in case of pair-end reads with F1R2 orientation and by $\{L_{n\ (reverse)}, L_{m\ (forward)}\}$ in case of pair-end reads with F2R1 orientation.

The resulting information may be recorded in a raw fragment-tagged read alignment file, such as a BAM or SAM format file. Using this file, it is possible to cluster groups of pair-end reads issued from the same fragment ligation from the alignment, so that downstream genomic analysis steps such as variant calling 153 can be performed by exploiting the information provided by PCR duplicates issued from the two strands of the original DNA fragment.

Variant Calling

Figure 8:
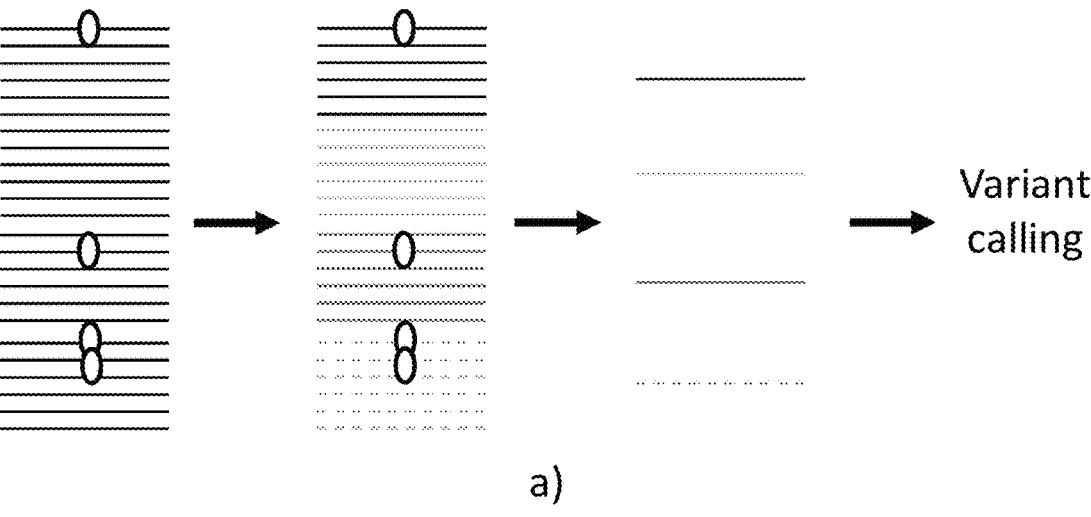
FIG. 8 shows an abstract representation of two different possible genomic analysis workflow steps to further identify variants out of the tagged reads according to the proposed methods.
Figure 8:
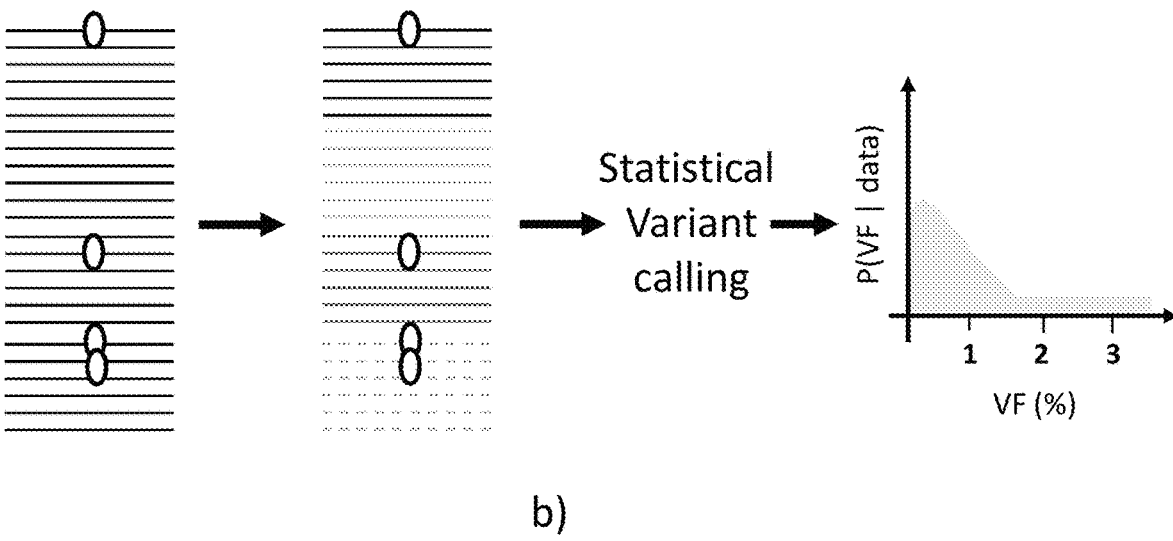

The resulting aligned reads may then be analyzed 153 to identify variants relative to the reference genome, such as SNVs, indels or structural variants (copy number variations, duplications, translocations). As illustrated by FIG. 8 and as reviewed for instance by Xu in *A review of somatic single nucleotide variant calling algorithms for next-generation sequencing data*, Computational and Structural Biotechnology Journal 16, pp. 15-24, February 2018, different approaches may be applied by the Genomic Data Analyzer 150. FIG. 8a) illustrates the consensus sequencing approach, in which a single polynucleotide sequence is collapsed out of each group of sequence reads sharing, in the aligned BAM file, the same alignment position and numerical code tag according to the proposed method. If group members disagree at certain positions, as represented by circles in FIG. 8a), various rules may be used to generate the consensus sequence which is then stored in a consensus BAM file (also known as read collapsed BAM file) as a single consensus aligned sequence read for each group of reads (family of reads corresponding to a parent fragment). The most frequently found base within the group may be kept as the consensus (simple majority rule). Quality scores may also be used to refine the consensus (weighted scoring). The resulting consensus sequence may then be processed by any conventional raw-reads-based variant callers. More generally, as will be apparent to those skilled in the art of NGS bioinformatics workflows, any consensus sequencing approach that is suitable as an intermediate step for collapsing the aligned reads into a single polynucleotide sequence prior to variant calling 153 may be used in combination with the proposed numerical code tag, similar to the processing of the UMI tag as in the public domain prior art methods reviewed by Xu, for instance with the MAGERI bioinformatics workflow (MAGERI: Computational pipeline for molecular-barcoded targeted resequencing, Shugay et al., PLoS Comput. Biol. 2017 May; 13 (5)), or in various commercial genomic data analysis workflows, for instance with the Illumina Read Collapsing step (https://support.illumina.com/help/BaseSpace_App_UMI_Error_Correction_OLH_1000000035906/Content/Source/Informatics/Apps/Read_Collapsing_appUMI.htm).

The above conventional consensus sequencing approaches however suffer from a number of limitations, which may be overcome by using more advanced genomic data analysis workflows based on advanced statistical modeling, such as data-driven methods derived from signal processing, or machine learning algorithms. FIG. 8b) illustrates probabilistic sequencing as an alternative embodiment to the consensus sequencing approach. In probabilistic sequencing, instead of producing a consensus BAM file at an intermediate step between alignment and variant calling, the Genomic Data Analyzer 150 may directly use the raw fragment-tagged alignment file to feed the raw groups of aligned reads as input to a statistical variant caller.

Instead of relying on consensus sequences obtained with heuristic rules (such as, e.g., a majority vote), this class of variant callers relies on statistical models describing how instrumental artefacts affects reads belonging to the same or to different families (or groups). The statistical model can for example incorporate the knowledge that:

in the presence of a mutated DNA molecule, the variant is supported by all reads issued from the two strands of that mutated molecule; sequencing errors can occur frequently, but independently across reads belonging or not to the same family;

PCR-errors are less frequent, but can affect multiple reads in the same family and rarely occur on both plus and minus strand of the same DNA molecule.

Analyzing the totality of reads within such a probabilistic framework allows, e.g., to compute the posterior probability of a variant allele frequency of interest. This posterior probability could then be used to, e.g., produce a variant call (e.g., if the probability of variant allele frequency>0 with probability p>threshold) and quantify its confidence level (i.e., the probability that the signal was generated by a real variant, rather than by instrumental noise).

One recently disclosed example of such a statistical variant caller is the SmCounter2 public domain stand-alone statistical variant caller which takes as input the aligned reads to calculate the variant probability in accordance with an error model based on a Beta distribution for the background error rates and a Beta-binomial distribution for the number of non-reference UMI outliers (smCounter2: an accurate low-frequency variant caller for targeted sequencing data with unique molecular identifiers, Xu et al., Bioinformatics, Vol., 35 (8), April 2019). smCounter2 accepts both a raw UMI-tagged BAM file and a consensused BAM file as input. In the proposed workflow, instead of the UMI tag the UMI-tagged BAM file may similarly include the numerical code tag of our proposed method, that is the pair of numerical values corresponding to the measured lengths of the variable adaptors ligated on each end of the ligated fragment according to the proposed wet lab method. Similar to SmCounter2, various variant callers from commercial workflows based on data-driven modeling, such as for instance the Sophia Genetics Data-Driven Medicine software (Sophia DDM) may also be adapted to individually call variants for each group of aligned reads issued from different DNA fragments based on the proposed numerical code tagging.

Exemplary Experiments

Experiment 1

Figure 9:
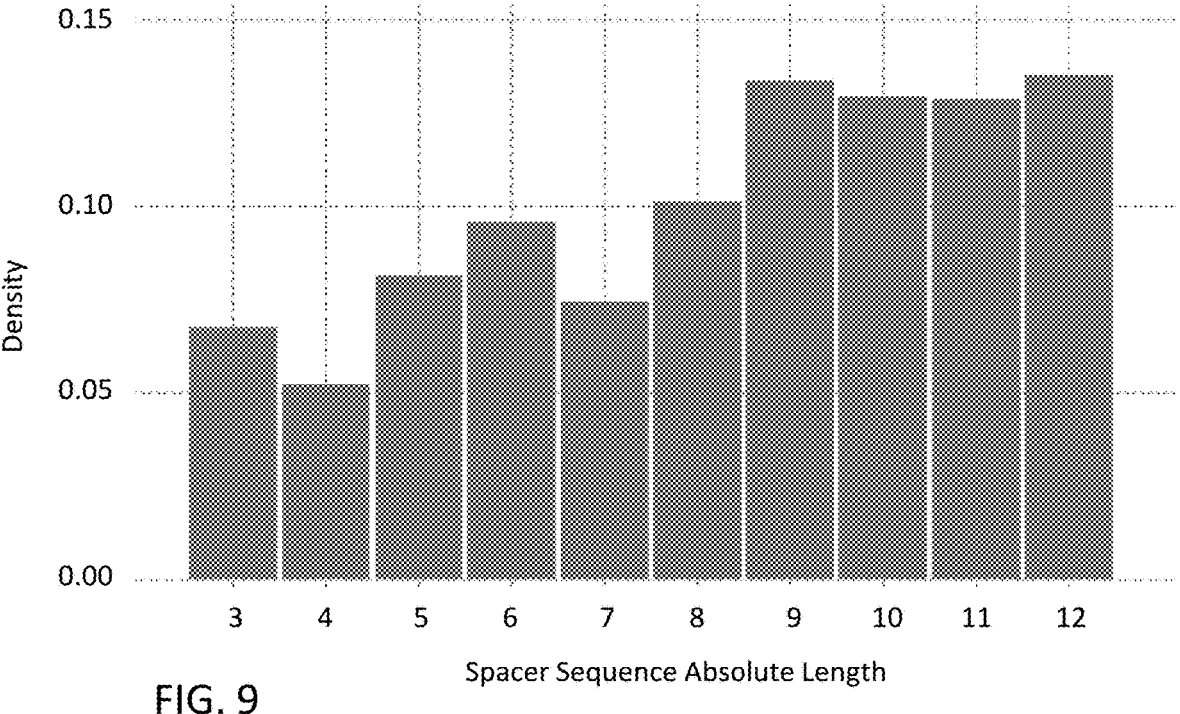
FIG. 9 shows the density distribution of each variable length adaptor in a library produced according to the proposed methods.

In a first experiment, we checked that all the proposed adaptors comprising a variable length spacer sequence as illustrated for instance in FIG. 5b) can be ligated to DNA fragments to generate a library of DNA-adaptor products. As illustrated by the measurement of FIG. 9, when using a reaction mixture with the proposed adaptors during the ligation reaction, all spacer sequences adaptors can be ligated to DNA fragments and are almost equally represented in the final DNA library.

Experiment 2

Figure 10:
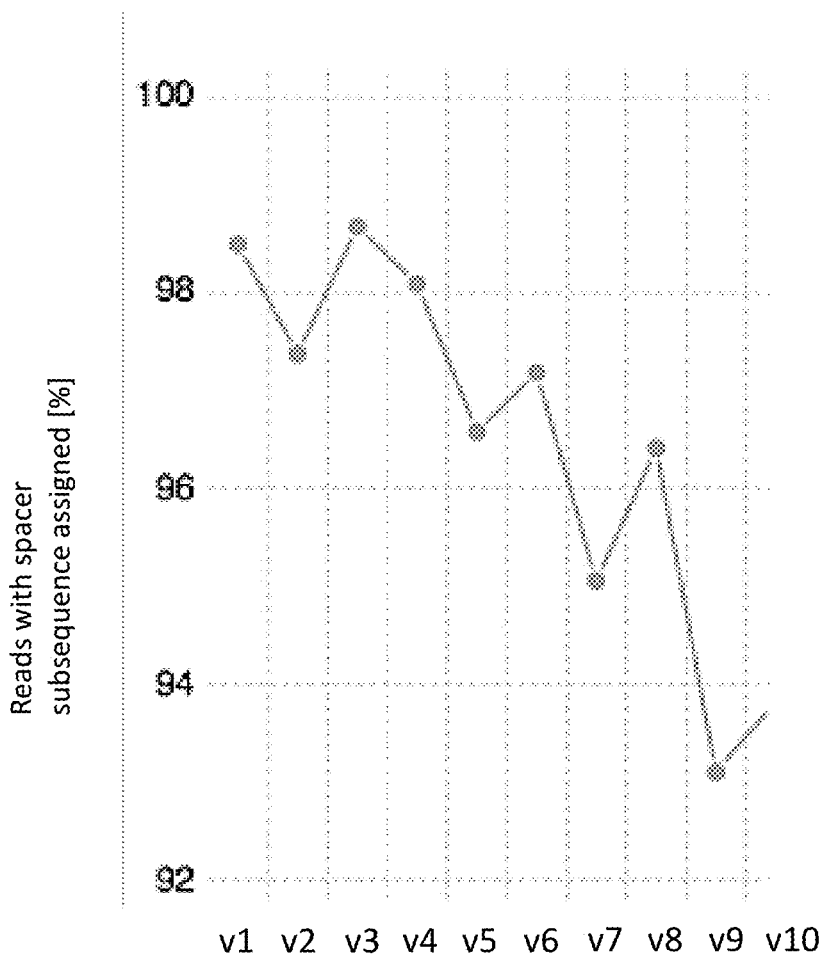
FIG. 10 shows the ratio of reads assigned to the expected adaptor sequences after sequencing.

In a second experiment, we checked that the library of DNA-adaptor products as generated with the first experiment can be sequenced on an NGS platform such as an Illumina NextSeq sequencer and decoded by a genomic data analyzer 150 such as the Sophia Genetics Data Driven Medicine (Sophia DDM) bioinformatics platform. Each spacer sequence can be decoded from the raw FASTQ files out of the sequencer by the Sophia Genetics Data Driven Medicine genomic data analyzer 150. The reads obtained show the expected sequence starting with the truncated spacer subsequence ending with the constant termination subsequence TS. FIG. 10 shows that even for the longest length adaptors (which are more prone to base calling errors) more than 93% of the reads can be assigned to the expected spacer sequence by the bioinformatics workflow. In average, it is possible to properly identify the spacer sequence (and thus measure its variable length to form the numerical code tag) for around 95% of the reads.

Experiment 3

In a third experiment, using the raw reads as sequenced in the second experiment, we have compared with the NGS data viewer their alignment results for a genomic analysis bioinformatics workflow (Sophia Genetics DDM v5) ignoring the numerical code tagging, that is, grouping the reads obtained for a specific genomic position solely based on their start and end positions out of the alignment (FIG. 11a), versus the same genomic analysis bioinformatics workflow further adapted to group the reads obtained for a specific genomic position based on their start and end positions out of the alignment as well as the additional fragment tagging information of the proposed method numerical code, made of the measured variable adaptor spacer sequence lengths on both ends of the fragments (FIG. 11b)).

Figure 11A:
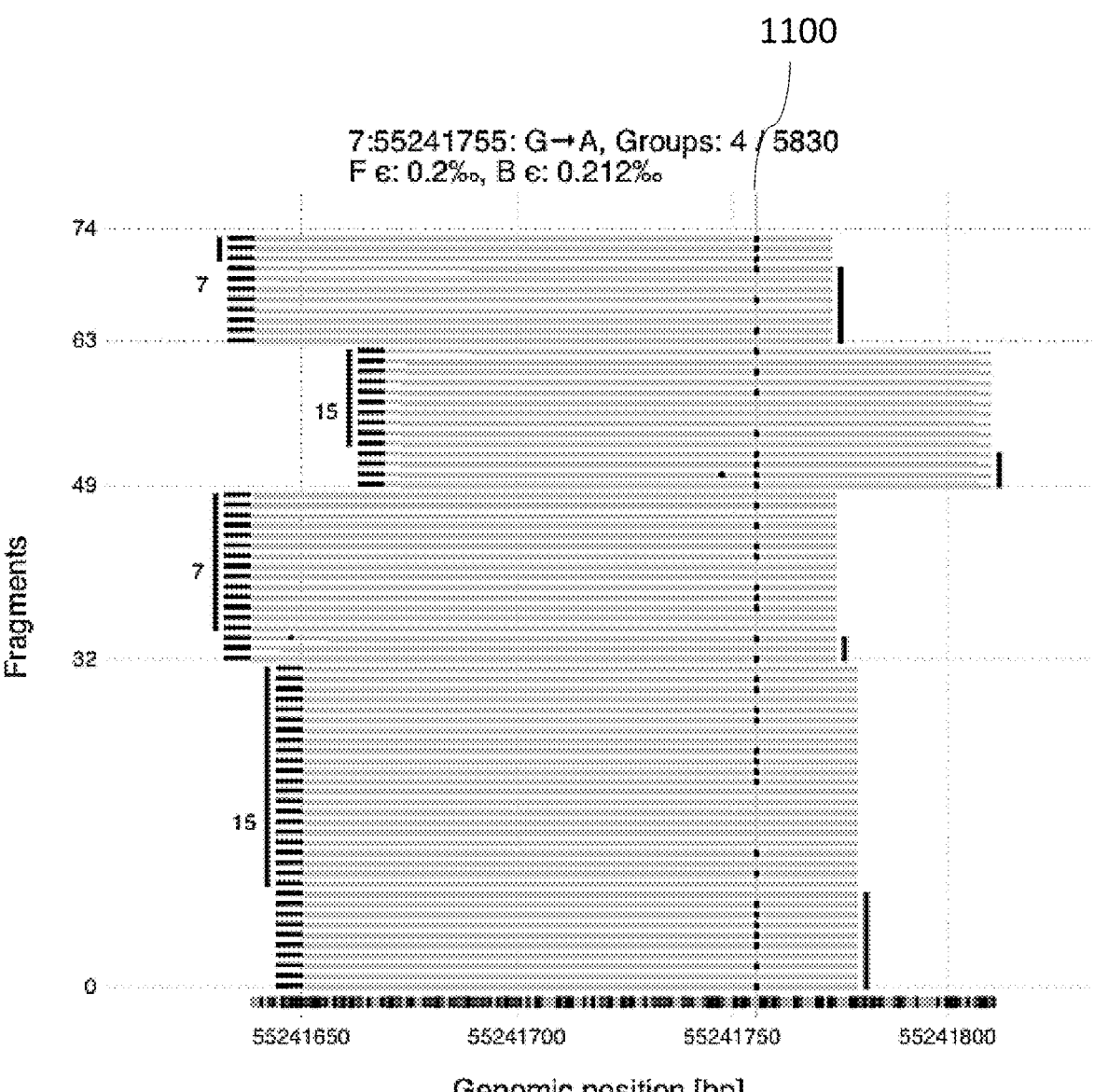
FIG. 11*a*) shows a NGS data viewer screen shot of reads aligned and grouped without taking into account the proposed adaptor numerical code tagging information, while FIG. 11*b*) shows a NGS data viewer screen shot of the same reads aligned and grouped according to the proposed adaptor numerical code tagging information to facilitate the identification of a heterogeneous SNP.
Figure 11B:
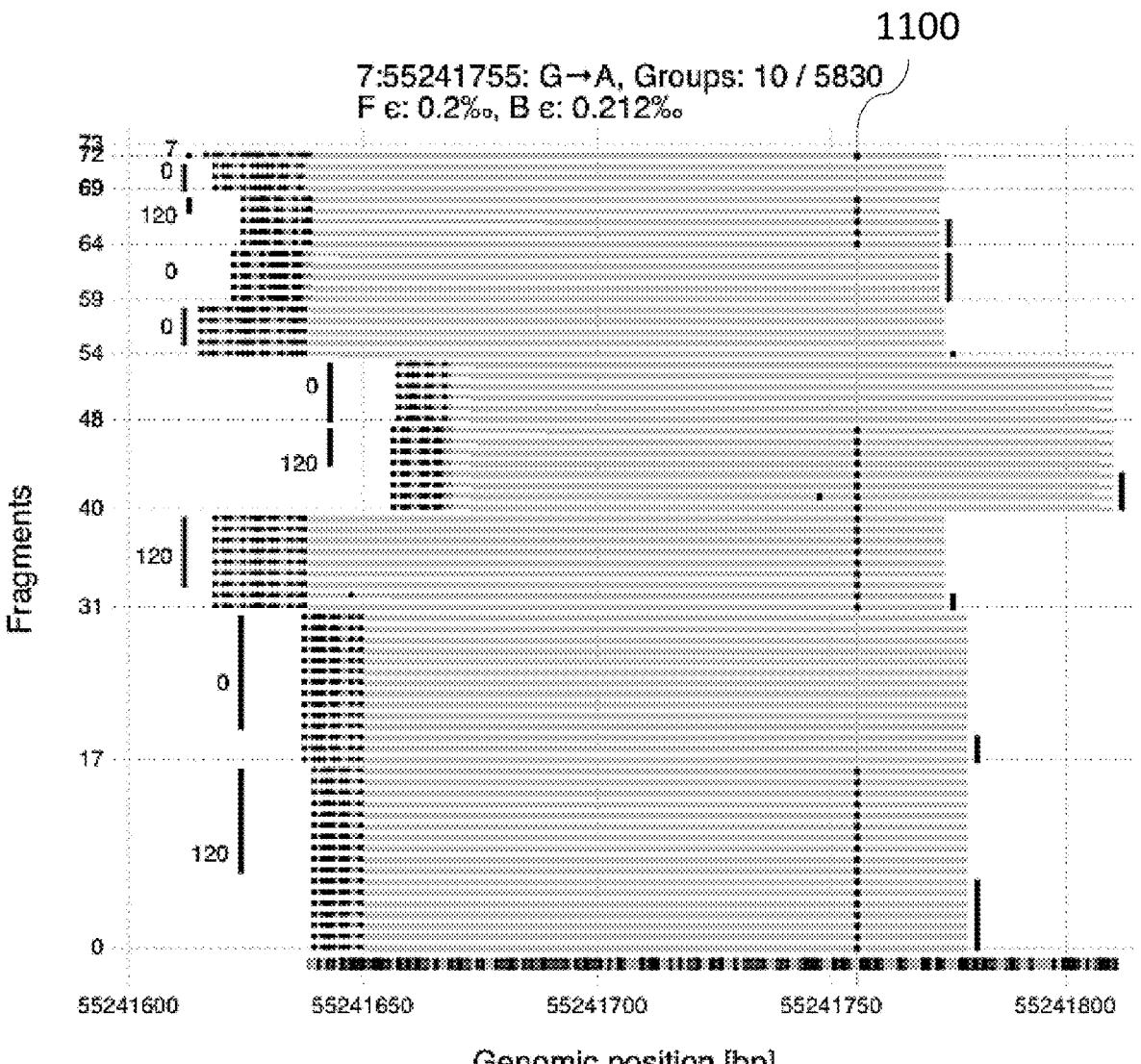

As can be seen on FIG. 11a) and FIG. 11b), the NGS data viewer highlights the genomic position 1100 of a heterozygous SNPs. In a group of PCR duplicates without discriminating the origin fragment, in theory all the reads should either display the SNP (and the downstream variant caller 153 should measure Variant Fraction=1) or not display it (and the downstream variant caller 153 should measure Variant Fraction=0). In our practical experiment however, as can be seen on FIG. 11a), only grouping the reads by their start and end information does not allow to accurately identify PCR duplicate groups as the actual variant fraction of the SNP differs from 0 or 1. This indicates that these groups contain DNA fragments deriving from at least two original DNA fragments. These original DNA fragments differed at the position of the SNP but were grouped together as they shared identical start and end positions. In contrast, as can be seen on FIG. 11b), adding the proposed numerical code as a tag allows to resolve these collisions by further subdividing and clustering the read groups of PCR duplicates having the same start and end positions into subsets originating from the same parent fragment according to their numerical code in the BAM file. In these subgroups, the Variant Fraction of the SNP can then be measured by the downstream variant caller 153 as either 0 or 1 as expected, thus demonstrating that the proposed numerical code in combination with the start and end position of the reads allows to discriminate PCR duplicates from colliding molecules.

Experiment 4

Motivation As will be apparent to those skilled in the art, calling variants at low variant allele fractions (VAF) is limited by sequencing errors and library preparation artefacts. A strategy to improve the analytical performance of NGS assays consists in exploiting the information provided by PCR duplicates for calling variants. Prior art solutions attempt to accurately identify PCR duplicate groups, for instance by mapping positions to identify PCR duplicates. However, the diversity of the shear points (and thus mapping positions) may not be sufficient to distinguish all original DNA molecules. Exogenous molecular barcodes have thus been introduced in order to provide additional information for the identification of PCR duplicate groups. However, there is no consensus today in the best industrial approach to generate such exogeneous barcodes, and a number of prior art solutions require the use of expensive library generation solutions, most of which have been primarily designed for use in a consensus sequencing workflow without benefiting from the most recent advances of probabilistic variant calling solutions. In contrast, the proposed variable length DNA-adaptors constructs aim at jointly facilitating both the exogenous identification of fragments and their efficient probabilistic genomic analysis to further improve the sensitivity and specificity of low frequency variant detection. This is demonstrated by a dedicated experiment, as will now be detailed.

Samples preparation—The nucleosomal DNA of six cell lines was spiked-in the nucleosomal DNA of a seventh cell line in different ratios in order to generate three samples with a series of single nucleotide variations (SNVs) at the following variant allele frequencies: 0.5-4%, 0.25-2% and 0.1-0.8%.

Targeted Library preparation Whole-genome libraries were prepared in duplicate from ng of each DNA mix using SOPHiA GENETICS library preparation kit following manufacturer s instructions with minor modifications. Briefly, after end-repair and A-tailing, the DNA fragments of each sample were ligated either to standard, non-barcoded, adaptors or to a set of variable length adaptors comprising a variable length spacer sequence as illustrated in FIG. 5b) ($L_{TS}$=3, $L_S$=9, so as to produce 10 different DNA adaptors of respective lengths 3 to 12 nucleotides). The libraries were then amplified using indexed, Illumina-compatible primers. Whole-genome libraries were captured using SOPHiA GENETICS capture protocol and a SOPHiA GENETICS catalog panel (footprint: 56 Kb) covering 23 of the SNVs present in the DNA mixes.

Data analysis The libraries from the variable length adaptors construction experiment were first pre-processed. The position of the constant subsequence at the beginning of the forward and reverse reads was determined. Then, the length of the adaptors present on both sides of each DNA fragment was used to generate a combinatorial code that was added to the read header prior to trimming the variable length adaptor sequences. Then, the reads of all libraries were aligned to the genome using the BWA-MEM aligner. Groups of PCR duplicates were identified using the fragment mapping position and the aforementioned combinatorial code. Variant calling was performed either by probabilistic sequencing or duplex consensus sequencing. For probabilistic sequencing, the posterior probability of the group of PCR duplicates being issued from a molecule carrying a SNV was computed and used to assign a quality score to each identified PCR duplicate group.

Results

FIG. 12 shows that the proposed variable length adaptors facilitate the detection of rate variants in artificial nucleosomal DNAs. FIG. 12a) shows the variant calling results for 3 samples (25 ng DNA input) analyzed in 1 replicates and harboring 23 SNVs at 3 distinct VAFs ranges (sample 1: 0.5-4%; sample 2: 0.25-2%; and sample 3: 0.1-0.8%) when prior art standard adaptors are used. FIG. 12b) shows the variant calling results obtained when the proposed variable length adaptors are used. Out of the 144 SNVs tested in this experiment, only 107 were detected when using standard adaptors. Using SLA libraries, the sensitivity improved with 123 variants being called. FIG. 12c) further compares the ROC curve showing the performance of variant calling in terms of true positive rate (TPR) versus false positive rate (FP) when respectively using probabilistic sequencing (dark grey) or duplex consensus sequencing (light grey) in the samples harbouring variants with VAF ranging between 0.1-0.8% and processed using the prior art standard adaptors. FIG. 12d) further compares the ROC curve showing the performance of variant calling in terms of true positive rate (TPR) versus false positive rate (FP) when respectively using probabilistic sequencing (dark grey) or duplex consensus sequencing (light grey) in the 2 samples harbouring variants with VAF ranging between 0.1-0.8% and processed using the proposed variable length adaptors.

Advantages of the Proposed Method

The proposed method thus facilitates the NGS bioinformatics identification of variants even out of low input DNA amounts while only requiring the ligation of a few predefined variable length adaptors to produce a library of DNA-adaptor products suitable for various downstream NGS workflows.

As will be apparent to those skilled in the art of high-throughput sequencing data processing, in the genomic analysis workflow the trimming of the adaptor sequence during read pre-processing need to be accurate, since over-trimming will lead to a loss of sequencing coverage and under-trimming can introduce sequencing artefacts. Prior art variable length adaptors that do not possess a constant termination subsequence signal (TS) do not allow to identify the boundary between the barcode and the beginning of the insert DNA fragment. As a result, they usually require trimming on the adaptor full length Lmax, and cause reduced coverage.

Moreover, the synthesis of adaptors being expensive, in a routine clinical practice workflow it is preferable use as many barcodes as required to resolve collisions for a specific application. When using a limited number of barcodes, it is important that those are uniformly represented in the final library, otherwise the effective number of barcode combination is reduced and may not suffice anymore. Having a constant termination subsequence TS at the extremity of each barcode prevents ligation sequence-specific biases and allows thus to have a more uniform barcode usage.

Furthermore, depending on the actual sequencing technology, for instance with Illumina sequencers, having base imbalance in the first sequencing cycles can reduce the sequencing quality. This can become an issue when using a limited number of random barcodes. Using predetermined sets of spacer sequences of variable length, that may be designed such as to have a balance base composition at each sequencing cycle, allows to maintain a high sequencing quality.

---

The invention claimed is:

1. A method for generating a library of DNA-adaptor products from at least two DNA fragments to facilitate the identification of the fragments in a high throughput sequencing data analysis workflow after amplification and sequencing, said method comprising:

generating a pool of adaptors that comprise a plurality of double-stranded or partially double-stranded polynucleotides comprising a spacer sequence on the double-stranded extremity of the adaptors, wherein the adaptors differ from each other by the total length of their spacer sequence of at least 3 and at most $L_{max}$ nucleotides, wherein each spacer sequence comprises a constant termination subsequence TS of length $L_{TS}$, wherein $L_{TS}$ comprises at least 3 nucleotides, concatenated with a variable spacer subsequence, and wherein the variable spacer subsequence is truncated from a common constant, predefined nucleotide sequence(S) having a length of $L_S$ nucleotides, wherein $L_S$ comprises 5-20 nucleotides, and wherein $L_{max}$ corresponds to the sum of $L_S$ and $L_{TS}$;

ligating, in a reaction mixture, a first and a second adaptor from the pool of adaptors to each end of a first double-stranded DNA fragment to produce a first DNA-adaptor product, wherein the ligation places the constant termination subsequence TS of each of the first and second adaptor between the double-stranded DNA fragment and the variable spacer subsequence of each of the first and second adaptor, respectively, so that the first DNA-adaptor product may be characterized by a numerical code formed by the respective lengths ($L_1$, $L_2$) of the first and the second adaptor spacer sequences ($SS_1$, $SS_2$); and ligating, in the same reaction mixture, a third and a fourth adaptor from the pool of adaptors to each end of a second double-stranded DNA fragment to produce a second DNA-adaptor product, wherein the ligation places the constant termination subsequence TS of each of the third and fourth adaptor between the double-stranded DNA fragment and the variable spacer subsequence of each of the third and fourth adaptor, respectively, so that the second DNA-adaptor product may be characterized by a numerical code formed by the respective lengths ($L_3$, $L_4$) of the third and the fourth adaptor spacer sequences ($SS_3$, $SS_4$), wherein determining whether the first DNA-adaptor product and second DNA-adaptor product correspond to different fragments relies on the placement of the constant termination subsequence between the double-stranded DNA fragment and the variable spacer subsequence and the characterization of the numerical code of the first and second DNA-adaptor product.

2. The method of claim 1, wherein the constant termination subsequence TS differs from the constant, predefined nucleotide sequence S by an edit distance of at least two.

3. The method of claim 1, wherein the spacer subsequence is truncated left to right from the start from said constant nucleotide sequence(S).

4. The method of claim 1, wherein the spacer subsequence is truncated right to left from the end from said constant nucleotide sequence(S).

5. The method of claim 1, wherein the constant termination subsequence TS is a triplet nucleotide ending with a T overhang to facilitate ligation to the DNA fragments.

6. The method of claim 1, wherein the constant termination subsequence TS is a quadruplet nucleotide ending with a T overhang to facilitate ligation to the DNA fragments.

7. The method of claim 1, further comprising:

amplifying the DNA-adaptor products to produce PCR duplicates suitable for high-throughput sequencing; and sequencing the PCR duplicates with a high-throughput sequencer to produce raw sequencing reads.

8. The method of claim 7, further comprising:

for each sequencing read Rn, trimming $L_{max}$ nucleotides from the beginning of the read, to produce a trimmed sequencing read;

recording the trimmed sequencing read in a pre-processed sequencing read file; and aligning to a reference genome the trimmed sequencing reads from the pre-processed sequencing read file, so as to map each trimmed read to a start position and an end position.

9. The method of claim 7, further comprising:

for each sequencing read Rn, searching for the constant termination subsequence TS in the first $L_{max}$ nucleotides of the sequencing read;

measuring the length $L_n$ of the spacer sequence $SS_{Rn}$ as the distance, in the number of nucleotides, between the start of the sequencing read Rn and the end of the constant termination subsequence TS;

trimming at least $L_n$ nucleotides from the beginning of the read, to produce a trimmed sequencing read;

recording the measured length $L_n$ and the trimmed sequencing read in a pre-processed sequencing read file; and aligning to a reference genome the trimmed sequencing reads from the pre-processed sequencing read file, so as to map each trimmed read to a start position and an end position.

10. The method of claim 9, wherein sequencing produces pair-end reads, further comprising:

tagging pair-end reads aligned to the same start and end position relative to the reference genome sequence reading direction and having the same numerical code pair of measured spacer sequence lengths ($L_1$, $L_2$), as sequencing reads potentially issued from the two strands of the same original double-stranded DNA fragment; and further subdividing those pair-end reads in two subgroups according to their strand of origin, where the numerical code pair of measured spacer sequence lengths ($L_1$, $L_2$) is given by $\{L_{n(forward)}, L_{n(reverse)}\}$ in case of pair-end reads with F1R2 orientation and by $\{L_{n(reverse)}, L_{n(forward)}\}$ in case of pair-end reads with F2R1 orientation.

11. The method of claim 10, further comprising collapsing each group of reads sharing the same start, end and numerical code into a consensus sequence for their parent fragment and identifying, with a variant calling method, variants for this parent fragment into the collapsed consensus sequence.

12. The method of claim 10, further comprising identifying for each group of reads sharing the same start, end and numerical code, with a statistical variant calling method, the probability of variants for their parent fragment.

13. The method of claim 1, wherein the method further includes a multiplex high throughput sequencing genomic analysis method for identifying genomic variants in at least two patient samples from a pool of samples, wherein the library of adaptors are different across samples.

14. The method of claim 13, wherein the library of adaptors differs across samples by the termination subsequence TS.

15. The method of claim 13, wherein the library of adaptors differs across samples by the predefined nucleotide sequence(S) used for truncating for the variable spacer subsequence.

\* \* \* \* \*

SEQUENCE LISTING

```
<160> NUMBER OF SEQ ID NOS: 8

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Based on human, animal, plant or microorganism

<400> SEQUENCE: 1
acaacactgt                                                          10

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Based on human, animal, plant or microorganism

<400> SEQUENCE: 2
cacaacactg t                                                        11

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Based on human, animal, plant or microorganism

<400> SEQUENCE: 3
ccacaacact gt                                                       12

<210> SEQ ID NO 4
<211> LENGTH: 11
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<223> OTHER INFORMATION: Based on human, animal, plant or microorganism

<400> SEQUENCE: 4
ccacaacctg t                                                          11

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Based on human, animal, plant or microorganism

<400> SEQUENCE: 5
ccacaactgt                                                            10

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccacaacact gtatgatt                                                   18

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
acaacactgt atgatt                                                     16

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ctgtatgatt                                                            10
```